United States Patent [19]

Toan et al.

[11] Patent Number: 5,869,588
[45] Date of Patent: Feb. 9, 1999

[54] POLYMERIC COMPOUNDS DERIVED FROM 2-HYDROXY-PHENYL-S-TRIAZINES SUBSTITUTED WITH ETHYLENICALLY UNSATURATED MOIETIES

[75] Inventors: Vien Van Toan, Lentigny; David George Leppard, Marly; Gerhard Rytz, Bern; Norbert Würms, St. Ursen; Pascal Hayoz, Villars-sur-Glâne, all of Switzerland

[73] Assignee: Ciba Specialty Chemicals Corporation, Tarrytown, N.Y.

[21] Appl. No.: 865,148

[22] Filed: May 29, 1997

Related U.S. Application Data

[62] Division of Ser. No. 535,406, Sep. 28, 1995, Pat. No. 5,672,704.

[30] Foreign Application Priority Data

Oct. 4, 1994 [CH] Switzerland ............................. 2989/94
Oct. 10, 1994 [CH] Switzerland ............................. 3039/94
Feb. 8, 1995 [CH] Switzerland ............................... 364/95

[51] Int. Cl.$^6$ ........................... C08F 26/06; C08F 26/08; C08K 5/34
[52] U.S. Cl. .......................... 526/261; 524/100; 526/263; 528/423
[58] Field of Search .................................. 526/261, 263; 528/423; 524/100

[56] References Cited

U.S. PATENT DOCUMENTS

| | | | |
|---|---|---|---|
| 3,244,708 | 4/1966 | Duennenberger et al. | 260/248 |
| 3,249,608 | 5/1966 | Biland et al. | 260/248 |
| 3,423,360 | 1/1969 | Huber et al. | 260/47 |
| 5,189,084 | 2/1993 | Birbaum et al. | 524/100 |
| 5,300,414 | 4/1994 | Leppard et al. | 430/507 |
| 5,364,749 | 11/1994 | Leppard et al. | 430/507 |

FOREIGN PATENT DOCUMENTS

| | | |
|---|---|---|
| 0434608 | 6/1991 | European Pat. Off. . |
| 0434619 | 6/1991 | European Pat. Off. . |
| 0530135 | 3/1993 | European Pat. Off. . |
| 6400983 | 8/1964 | Netherlands . |
| 481954 | 1/1970 | Switzerland . |
| 484695 | 3/1970 | Switzerland . |
| 1256051 | 12/1971 | United Kingdom . |

OTHER PUBLICATIONS

Chemical Abstract 119:213929, 1993.
Chemical Abstract 121590N of CH 484695, 1970.

*Primary Examiner*—Yogendra N. Gupta
*Attorney, Agent, or Firm*—Luther A. R. Hall

[57] ABSTRACT

The invention relates to novel 2-hydroxyphenyltriazines and to homopolymers and copolymers obtainable therefrom, as described in greater detail in claims 1 and 5; the novel compounds can be used as UV absorbers in or for organic materials.

7 Claims, No Drawings

POLYMERIC COMPOUNDS DERIVED FROM 2-HYDROXY-PHENYL-S-TRIAZINES SUBSTITUTED WITH ETHYLENICALLY UNSATURATED MOIETIES

This is a divisional of application Ser. No. 08/535,406, filed on Sep. 28, 1995, now U.S. Pat. No. 5,672,704, issued on Sep. 30, 1997.

The present invention relates to novel 2-hydroxyphenyltriazines, to a process for their preparation, and to their use as UV absorbers in organic materials.

EP-A-0 434 608 discloses UV absorbers of the hydroxyphenyltriazine type, in particular in combination with sterically hindered amines. Further compounds of this type are described, for example, in U.S. Pat. No. 5,189,084, EP-A-0 530 135, U.S. Pat. No. 5,364,749 and U.S. Pat. No. 5,300,414.

It is furthermore known to use UV absorbers of the hydroxyphenyltriazine type in, for example, surface coatings. U.S. Pat. No. 3,423,360 describes polymeric hydroxyphenyltriazine acrylates and methacrylates and their use in surface coatings.

However, the known UV absorbers frequently have undesired properties, for example inadequate inherent stability to light, heat or moisture, migration or volatility, resistance to emulsification, formation of crystals, or caking.

A group of 2-hydroxyphenyltriazine UV absorbers has now been found which, surprisingly, satisfies industrial requirements to a considerable extent.

Combinations of the novel 2-hydroxyphenyltriazines with UV absorbers of other types, such as benzophenones, benzotriazoles, sterically hindered amines, oxanilides, cyanoacrylates, salicylates, acrylonitrile or thiazolines, are also suitable for stabilizing organic materials.

The present application thus relates to 2-hydroxyphenyltriazines of the formula I in which $E_1$ and $E_2$, independently of one another, are a group of the formula Ia or Ib in which A is —C(=O)—$CR_5$=CH—$R_6$;

$R_1$ is —CH(OA)(CH$_2$)(CH$_2$)(CH$_2$)$_m$—, —CH$_2$—[phenyl ring]—C(=CH$_2$)—$R_{10}$, —CH$_2$—C(=CH$_2$)—$R_{10}$, —(CH$_2$)$_p$—SiR$_{11}$R$_{11}$'—CH=CH$_2$, —C(=O)—(CH$_2$)$_q$—CH=CH$_2$ or —C(=O)—O—CH$_2$—C(=CH$_2$)—$R_{10}$;

in the case where $R_3$' is —O—$CR_8R_8$'—(CH$_2$)$_1$—XA, $R_1$ can additionally be $C_1$–$C_{18}$alkyl or $C_3$–$C_{20}$alkyl interrupted by —O—, —CO—O— or —O—CO—; and, in the case where $E_1$ is a group of the formula Ia in which neither of the radicals $R_2$ and $R_{14}$ is hydrogen, $R_1$ can additionally be —A, —CH$_2$—CH(XA)—CH$_2$—O—$R_7$, —$CR_8R_8$'—(CH$_2$)$_1$—XA, —CH$_2$—CH(OA)—$R_9$, —CH$_2$—CH(OH)—CH$_2$—XA, —CHR$_8$—(CH$_2$)$_r$—C(=O)—O—CH$_2$—CH(OH)—CH$_2$—OA and —$CR_8R_8$'—(CH$_2$)$_1$—C(=O)—XA; and, in the case where $E_1$ is a group of the formula Ib, $R_1$ can additionally be —CH$_2$—CH(XA)—CH$_2$—O—$R_7$;

$R_2$, independently of one another, are H, $C_1$–$C_{12}$alkyl, cyclohexyl, $C_3$–$C_6$alkenyl, halogen, phenyl or trifluoromethyl;

$R_2$', independently of one another, are $C_1$–$C_{18}$alkoxy, $C_3$–$C_{18}$alkenoxy, —OH or —O—CO—$R_{12}$;

$R_3$ and $R_3$', independently of one another, are H, —OH, —O—CH$_2$—CH(XA)—CH$_2$—O—$R_7$, —O—(CH$_2$)$_p$—SiR$_{11}$R$_{11}$'—CH=CH$_2$, —O—C(=O)—(CH$_2$)$_q$—CH=CH$_2$, —O—C(=O)—O—CH$_2$—C(=CH$_2$)—$R_{10}$, —O—$CR_8R_8$'—(CH$_2$)$_1$—XA, —O—CH$_2$—CH(OA)—$R_9$, —O—CH$_2$—CH(OH)—CH$_2$—XA, —O—CHR$_8$—(CH$_2$)$_r$—C(=O)—O—CH$_2$—CH(OH)—CH$_2$—OA, —$CR_8R_8$'—(CH$_2$)$_1$—C(=O)—XA, $C_1$–$C_{18}$alkyl, $C_6$–$C_{12}$cycloalkyl, $C_3$–$C_{18}$alkenyl, —OR$_{131}$, halogen, trifluoromethyl, phenyl, phenyl-$C_1$–$C_4$alkyl, —CN, $C_1$–$C_{18}$alkyl-S(=O)$_t$— or phenyl-S(=O)$_t$—;

$R_4$, $R_4$' and $R_4$", independently of one another, are H, $C_1$–$C_{18}$alkyl, $C_3$–$C_6$alkenyl, —OR$_{131}$, halogen, trifluoromethyl, phenyl, phenyl-$C_1$–$C_4$alkyl, mono- to tri-$C_1$–$C_4$alkyl-substituted phenyl-$C_1$–$C_4$alkyl, —CN, $C_1$–$C_{18}$alkyl-S(=O)$_t$— or phenyl-S(=O)$_t$—;

$R_5$ is H, —CH$_2$—COOR$_{13}$, $C_1$–$C_4$alkyl or —CN;

$R_6$ is H, —COOR$_{13}$, $C_1$–$C_{17}$alkyl or phenyl;

$R_7$ is $C_1$–$C_{18}$alkyl; $C_5$–$C_{12}$cycloalkyl; $C_3$–$C_{18}$alkenyl; phenyl; phenyl which is substituted by one to three $C_1$–$C_8$alkyl, $C_1$–$C_8$alkoxy, $C_3$–$C_8$alkenoxy, halogen or trifluoromethyl radicals; phenyl-$C_1$–$C_4$alkyl; $C_3$–$C_{50}$alkyl which is interrupted by one or more —O—; 1-adamantyl; 2-adamantyl; norbornyl; 2-methylnorbornyl or —C(=O)—$R_{12}$;

$R_8$ and $R_8'$, independently of one another, are H, $C_1$–$C_{18}$alkyl, phenyl, phenyl-$C_1$–$C_8$alkyl, or phenyl substituted by 1 to 3 $C_1$–$C_4$alkyl, $C_3$–$C_8$alkenoxy, $C_1$–$C_8$alkoxy, halogen or $CF_3$ radicals;

$R_9$ is $C_1$–$C_{18}$alkyl, phenyl or phenyl-$C_1$–$C_4$alkyl;

$R_{10}$ is H or —$CH_3$;

$R_{11}$ and $R_{11}'$, independently of one another, are $C_1$–$C_4$alkyl or phenyl or phenyl which is substituted by one to three $C_1$–$C_8$alkyl, $C_1$–$C_8$alkoxy, $C_3$–$C_8$alkenoxy, halogen or trifluoromethyl radicals;

$R_{12}$ is H, $C_1$–$C_{18}$alkyl, $C_2$–$C_{18}$alkenyl, phenyl, phenyl-$C_1$–$C_4$alkyl, $C_5$–$C_{12}$cycloalkyl, $C_1$–$C_{12}$alkoxy, phenoxy, norborn-2-yl, 5-norbornen-2-yl or 1-adamantyl;

$R_{13}$ is H, $C_1$–$C_{18}$alkyl, $C_3$–$C_{18}$alkenyl, phenyl, $C_5$–$C_{12}$cycloalkyl, $C_3$–$C_{50}$alkyl which is interrupted by one or more —O—, phenyl which is substituted by one to three $C_1$–$C_8$alkyl, $C_1$–$C_8$alkoxy, $C_3$–$C_8$alkenoxy, halogen or trifluoromethyl radicals, phenyl-$C_1$–$C_4$alkyl, 1-adamantyl, 2-adamantyl, norbornyl or 2-methylnorbornyl;

$R_{14}$ and $R_{15}$, independently of one another, are H, $C_1$–$C_{18}$alkyl, $C_3$–$C_{18}$alkenyl, $C_6$–$C_{12}$cycloalkyl, halogen, $CF_3$, phenyl, phenyl-$C_1$–$C_4$alkyl, CN, $C_1$–$C_{18}$-alkyl-S(=O)$_t$—, phenyl-S(=O)$_t$— or —$OR_{131}$;

$R_{131}$ is $C_1$–$C_{18}$alkyl, $C_3$–$C_{18}$alkenyl, $C_1$–$C_{18}$alkyl which is substituted by OH, $C_1$–$C_{18}$alkoxy, $C_5$–$C_{12}$cycloalkoxy, $C_3$–$C_6$alkenyloxy, halogen, —$COOR_{13}$, —$CONH_2$, —$COHNR_{132}$, —$CON(R_{132})(R_{133})$, —$NHCOR_{12}$, —CN, —$OCOR_{12}$, phenoxy and/or by phenoxy which is substituted by $C_1$–$C_{18}$alkyl, $C_1$–$C_{18}$alkoxy or halogen; or is $C_3$–$C_{18}$alkenyl; $C_6$–$C_{12}$cycloalkyl; $C_1$–$C_4$alkyl- and/or —$OCOR_{12}$-substituted $C_6$–$C_{12}$cycloalkyl; $C_3$–$C_{50}$alkyl which is interrupted by one or more —O— and which is unsubstituted or substituted by OH or O—CO—$R_{12}$; phenyl; phenyl-$C_1$–$C_4$alkyl; —$COR_{12}$ or —$SO_2R_{12}$;

$R_{132}$ and $R_{133}$, independently of one another, are $C_1$–$C_{12}$alkyl, $C_3$–$C_{12}$alkoxyalkyl, $C_4$–$C_{16}$dialkylaminoalkyl or $C_5$–$C_{12}$cycloalkyl; or $R_{132}$ and $R_{133}$ together are $C_3$–$C_9$alkylene, $C_3$–$C_9$oxaalkylene or -azaalkylene;

X is —$NR_8$—, —O—, —NH—($C_nH_{2n}$)—NH— or —O—($C_kH_{2k}$)—NH—;

k is a number from 2 to 4;

l is a number from 0 to 19;

m is a number from 2 to 8;

n is a number from 0 to 4;

p is a number from 0 to 10;

q is a number from 1 to 8;

r is a number from 0 to 18; and t is the number 0, 1 or 2.

Substituents in the compounds of the formula (I) which are alkyl having up to 18 carbon atoms are radicals such as methyl, ethyl, propyl, butyl, pentyl, hexyl, heptyl, octyl, nonyl, decyl, undecyl, dodecyl, tetradecyl, hexadecyl or octadecyl, or the corresponding branched isomers.

Substituents in the compounds of the formula (I) which are alkoxy having up to 18 carbon atoms are radicals such as methoxy or ethoxy, or radicals analogous to the above alkyl radicals.

Substituents in the compounds of the formula (I) which are alkenyl having up to 18 carbon atoms are radicals such as vinyl, prop-1-enyl (—CH=CH—$CH_3$) or prop-2-enyl (—$CH_2$—CH=$CH_2$), or radicals analogous to the above alkyl radicals.

Substituents in the compounds of the formula (I) which are alkenoxy having up to 18 carbon atoms are radicals such as prop-1-enoxy (—O—CH=CH—$CH_3$) or prop-2-enoxy (—O—$CH_2$—CH=$CH_2$), or radicals analogous to the above alkyl radicals.

Substituents in the compounds of the formula (I) which are phenyl-$C_1$–$C_4$alkyl or mono- to tri-$C_1$–$C_4$alkyl-substituted phenyl-$C_1$–$C_4$alkyl are radicals such as

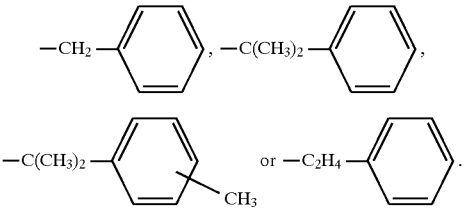

Substituents in the compounds of the formula (I) which are phenyl-$C_1$–$C_4$alkoxy are radicals such as

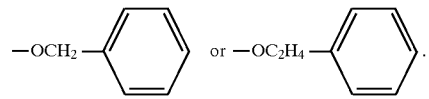

Substituents in the compounds of the formula (I) which are halogen are fluorine, chlorine, bromine or iodine.

$R_1$ is preferably —$CH_2$—CH(OA)—$CH_2$—O—$R_7$ or

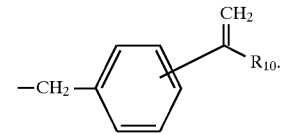

$R_2$ is preferably H, $C_1$–$C_4$alkyl, $C_3$alkenyl, F, Cl or phenyl; particularly preferably H, —$CH_3$ or Cl; and very particularly preferably H or —$CH_3$.

$R_2'$ is preferably —OH, $C_1$–$C_4$alkoxy or $C_3$alkenoxy; particularly preferably —OH, $C_1$–$C_2$alkoxy or $C_3$alkenoxy; and very particularly preferably —OH.

$R_3$ and $R_3'$ are preferably —O—$CH_2$—CH(OA)—$CH_2$—O—$R_7$,

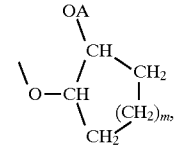

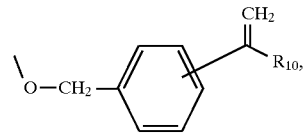

O—$CR_8R_8'$—($CH_2$)$_l$—OA, —O—$CH_2$—CH(OA)—$R_9$, —O—$CH_2$—CH(OH)—$CH_2$—XA, H, —OH, $C_1$–$C_4$alkyl, cyclohexyl, $C_3$alkenyl, $C_1$–$C_4$alkoxy, $C_3$alkenoxy, F, Cl, trifluoromethyl, phenyl, phenoxy, benzyl, benzoxy or —CN;

particularly preferably H, —OH, —O—CH$_2$—CH(OA)—CH$_2$—O—R$_7$,

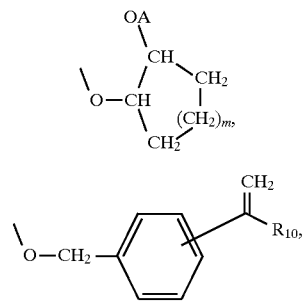

—O—CH$_2$—(CH$_2$)$_1$—OA, —CH$_3$, C$_1$-C$_4$alkoxy, C$_3$alkenoxy, F, Cl, phenyl, benzoxy or —CN; and very particularly preferably H, —OH, —O—CH$_2$—CH(OA)—CH$_2$—O—R$_7$,

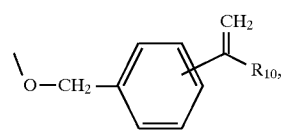

—O—CH$_2$—(CH$_2$)$_1$—OA, —CH$_3$, —OCH$_3$, Cl, phenyl or —CN.

R$_4$, R$_4$' and R$_4$" are preferably H, C$_1$-C$_4$alkyl, C$_3$alkenyl, C$_1$-C$_4$alkoxy, C$_3$alkenoxy, F, Cl, trifluoromethyl, phenyl, phenyl-C$_1$-C$_3$alkyl or —CN; particularly preferably H, —CH$_3$, C$_3$alkenyl, —OCH$_3$, C$_3$alkenoxy, F, Cl, phenyl-C$_3$alkyl or —CN; and very particularly preferably H or —CH$_3$.

R$_5$ is preferably H or —CH$_3$.

R$_6$ is preferably H, —COOR$_{13}$, —CH$_3$ or phenyl; and particularly preferably H or —CH$_3$.

R$_7$ is preferably C$_1$-C$_8$alkyl, cyclohexyl, C$_3$-C$_8$alkenyl, phenyl, phenyl which is substituted by one to three C$_1$-C$_4$alkyl or C$_1$-C$_4$alkoxy radicals, or benzyl, and particularly preferably C$_1$-C$_8$alkyl, cyclohexyl, C$_3$alkenyl, phenyl or benzyl.

R$_8$ and R$_8$' are preferably, independently of one another, H or C$_1$-C$_8$alkyl.

R$_{10}$ is preferably hydrogen.

R$_{11}$ and R$_{11}$', independently of one another, are preferably C$_1$-C$_4$alkyl or phenyl, especially methyl.

X is preferably —O— or —NR$_8$—, particularly an oxygen atom.

The value of the index 1 is preferably 1–15.

Compounds of the formula I which can be employed in accordance with the invention therefore conform, for example, to the formula Ic

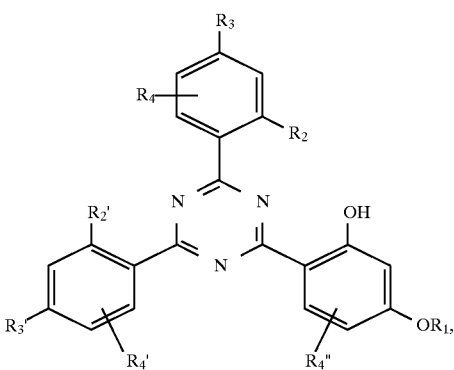

in which

A is —C(=O)—CR$_5$=CH—R$_6$;

R$_1$, independently of one another, are

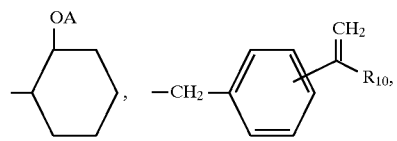

—CH$_2$—C(=CH$_2$)—R$_{10}$, —(CH$_2$)$_p$—SiR$_{11}$R$_{11}$'—CH=CH$_2$, —C(=O)—(CH$_2$)$_q$—CH=CH$_2$ or —C(=O)—O—CH$_2$—C(=CH$_2$)—R$_{10}$; and, in the case where R$_2$' is OH or OA, R$_1$ can additionally be —CH$_2$—CH(OA)—CH$_2$—O—R$_7$;

R$_2$ and R$_2$', independently of one another, are H, —OH, —OA, C$_1$-C$_{12}$alkyl, cyclohexyl, C$_3$-C$_6$alkenyl, C$_1$-C$_{18}$alkoxy, C$_2$-C$_{18}$alkenoxy, halogen, phenyl or trifluoromethyl;

R$_3$ and R$_3$', independently of one another, are H, —OH, —OA, the abovementioned —OR$_1$, —O—CHR$_8$—(CH$_2$)$_1$—OA, —O—CH$_2$—CH(OA)—R$_9$, —O—CH$_2$—CH(OH)—CH$_2$—OA, —O—CHR$_8$—(CH$_2$)$_r$—C(=O)—O—CH$_2$—CH(OH)—CH$_2$—OA, C$_1$-C$_{12}$alkyl, cyclohexyl, C$_3$-C$_6$alkenyl, C$_1$-C$_{18}$alkoxy, C$_3$-C$_{18}$alkenoxy, halogen, trifluoromethyl, phenyl, phenoxy, phenyl-C$_1$-C$_4$alkyl, phenyl-C$_1$-C$_4$alkoxy, —CN, C$_1$-C$_{18}$alkyl-S(=O)$_t$— or phenyl-S(=O)$_t$—;

R$_4$, R$_4$' and R$_4$", independently of one another, are H, C$_1$-C$_{12}$alkyl, C$_3$-C$_6$alkenyl, C$_1$-C$_{18}$alkoxy, C$_3$-C$_{18}$alkenoxy, halogen, trifluoromethyl, phenyl, phenoxy, phenyl-C$_1$-C$_4$alkyl, mono- to tri-C$_1$-C$_4$alkyl-substituted phenyl-C$_1$-C$_4$alkyl, phenyl-C$_1$-C$_4$alkoxy, —CN, C$_1$-C$_{18}$alkyl-S(=O)$_t$— or phenyl-S(=O)$_t$—;

R$_5$ is H, —CH$_2$—COOR$_3$, C$_1$-C$_4$alkyl or —CN;

R$_6$ is H, —COOR$_{13}$, C$_1$-C$_{17}$alkyl or phenyl;

R$_7$ is C$_1$-C$_{18}$alkyl, cyclohexyl, C$_3$-C$_{18}$alkenyl, phenyl, phenyl which is substituted by one to three C$_1$-C$_8$alkyl, C$_1$-C$_8$alkoxy, C$_2$-C$_8$alkenoxy, halogen or trifluoromethyl radicals, phenyl-C$_1$-C$_4$alkyl or —C(=O)—R$_{12}$;

R$_8$ is H or C$_1$-C$_{18}$alkyl;

R$_9$ is C$_1$-C$_{18}$alkyl, phenyl or phenyl-C$_1$-C$_4$alkyl;

R$_{10}$ is H or —CH$_3$;

R$_{11}$ and R$_{11}$', independently of one another, are C$_1$-C$_4$alkyl or phenyl or phenyl which is substituted by one to three C$_1$-C$_8$alkyl, C$_1$-C$_8$alkoxy, C$_3$-C$_8$alkenoxy, halogen or trifluoromethyl radicals;

$R_{12}$ is $C_1$–$C_{18}$alkyl, $C_2$–$C_{18}$alkenyl or phenyl;

$R_{13}$ is H, $C_1$–$C_{18}$alkyl, $C_3$–$C_{18}$alkenyl or phenyl;

l is a number from 0 to 19;

p is a number from 0 to 10;

q is a number from 1 to 8;

r is a number from 0 to 18; and t is the number 0, 1 or 2.

Preference is given to compounds of the formula (I) in which $R_2$ is H, $C_1$–$C_4$alkyl, $C_3$alkenyl, F, Cl or phenyl;

$R_2'$ is $C_1$–$C_4$alkoxy, $C_3$alkenoxy, —O—CO—$R_{12}$ or —OH;

$R_3$ and $R_3'$, independently of one another, are H, —OH, —O—$CH_2$—CH(XA)—$CH_2$—O—$R_7$,

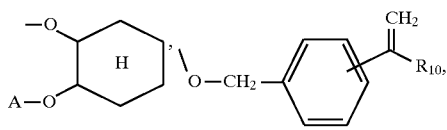

—O—$CHR_8$—$(CH_2)_l$—XA, —O—$CH_2$—CH(OA)—$R_9$, —O—$CH_2$—CH(OH)—$CH_2$—XA, $C_1$–$C_4$alkyl, cyclohexyl, $C_3$alkenyl, —$OR_{131}$, F, Cl, trifluoromethyl, phenyl, benzyl or —CN;

$R_4'$ and $R_4''$, independently of one another, are H, $C_1$–$C_4$alkyl, $C_3$alkenyl, $C_1$–$C_4$alkoxy, $C_3$alkenoxy, F, Cl, trifluoromethyl, phenyl, phenyl-$C_1$–$C_3$alkyl or —CN;

$R_5$ is H or —$CH_3$;

$R_6$ is H, —$COOR_{13}$, —$CH_3$ or phenyl;

$R_7$ is $C_1$–$C_8$alkyl, cyclohexyl, $C_3$–$C_8$alkenyl, phenyl, phenyl which is substituted by one to three $C_1$–$C_4$alkyl or $C_1$–$C_4$alkoxy radicals, or benzyl;

$R_9$ is $C_1$–$C_{10}$alkyl, phenyl or benzyl;

$R_{11}$ and $R_{11}'$, independently of one another, are $C_1$–$C_4$alkyl or phenyl;

$R_{12}$ is H, $C_1$–$C_{18}$alkyl, $C_2$–$C_3$alkenyl, phenyl, phenyl-$C_1$–$C_4$alkyl or cyclohexyl;

$R_{13}$ is $C_1$–$C_4$alkyl, $C_3$alkenyl, cyclohexyl, phenyl-$C_1$–$C_4$alkyl or phenyl;

$R_4$, $R_{14}$ and $R_{15}$, independently of one another, are H, $C_1$–$C_8$alkyl, F, Cl, $C_1$–$C_4$alkoxy, $CF_3$, phenyl, or CN;

$R_{131}$ is $C_1C_{18}$alkyl, $C_3$–$C_{18}$alkyl which is substituted by OH, $C_1$–$C_{18}$alkoxy, $C_5$–$C_{12}$cycloalkoxy, —$COOR_{13}$, —$CONH_2$, —$COHNR_{132}$, —$CON(R_{132})(R_{133})$, —$NHCOR_{12}$, —CN, —$OCOR_{12}$ and/or phenoxy, or is $C_3$alkenyl, $C_6$–$C_{12}$cycloalkyl, $C_3$–$C_{50}$alkyl which is interrupted by one or more —O— and may be substituted by OH or $OCOR_{12}$; phenyl, phenyl-$C_1$–$C_4$alkyl, —$COR_{12}$ or —$SO_2R_{12}$;

X is —O— or —$NR_8$—;

l is a number from 1 to 19; and r is a number from 0 to 10.

Of these, preference is given to particular compounds of the formula (I), in which $E_1$ and $E_2$, independently of one another, are a group of the formula Ia or Ib and in which

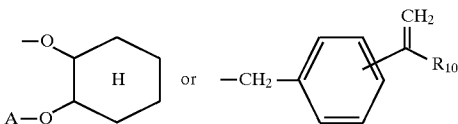

or in the case where $R_3'$ is —O—$CR_8R8'$—$(CH_2)_l$—XA, $R_1$ can additionally be $C_1$–$C_{12}$alkyl or $C_6$–$C_{18}$ alkyl which is interrupted by —O—, —CO—O— or —O—CO—; and, in the case where $E_1$ is a group of the formula Ib, $R_1$ can additionally be —$CH_2$—CH(XA)—$CH_2$—O—$R_7$; and in the case where $E_1$ is a group of the formula Ia in which neither of the radicals $R_2$ and $R_{14}$ is hydrogen, $R_1$ can additionally be —$CH_2$—CH(XA)—$CH_2$—O—$R_7$, —$CR_8R'_8$—$(CH_2)_l$—XA, —$CH_2$—CH(OA)—$R_9$ and —$CH_2$—CH(OH)—$CH_2$—XA;

$R_2$ is H, —$CH_3$ or Cl; $R_2'$ is —OH;

$R_3$ is H, —$CH_3$, $C_1$–$C_4$alkoxy, $C_3$alkenoxy, F, Cl, phenyl, benzoxy or —CN;

$R_3'$ is —OH, —O—$CH_2$—CH(XA)—$CH_2$—O—$R_7$,

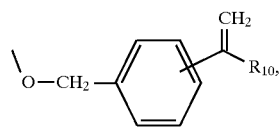

—O—$CH_2$—$(CH_2)_l$—XA, —O—$CH_2$—CH(OA)—$R_9$, —O—$CH_2$—CH(OH)—$CH_2$—XA, or —$OR_{131}$;

$R_4$, $R_{14}$ and $R_{15}$, independently of one another, are H, F, Cl, $OCH_3$ or $CH_3$;

$R_4'$ and $R_4''$ stand in meta-position to the triazine ring and, independently of one another, are H, —$CH_3$, $C_3$alkenyl, —$OCH_3$, $C_3$alkenoxy, F, Cl, phenyl-$C_3$alkyl or —CN;

$R_5$ is H or —$CH_3$;

$R_6$ is H;

$R_7$ is $C_1$–$C_8$alkyl, cyclohexyl, $C_3$alkenyl, phenyl or benzyl;

$R_8$ and $R_8'$ are H;

$R_9$ is $C_1$–$C_{10}$alkyl;

$R_{12}$ is $C_1$–$C_{18}$alkyl, phenyl or cyclohexyl;

$R_{131}$ is $C_3$–$C_{18}$alkyl or $C_3$–$C_{18}$alkyl which is substituted by OH, $C_1$–$C_{18}$alkoxy, —$NHCOR_{12}$ and/or —$OCOR_{12}$; and l is a number from 1 to 19.

The invention also relates to polymeric compounds obtainable by addition polymerization of at least one compound of the formula (Id) or at least one compound of the formula (Id) and at least one further ethylenically unsaturated compound

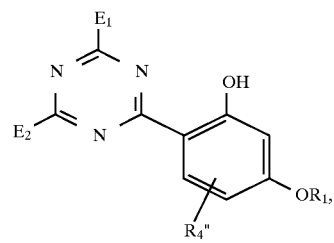

(Id)

in which $E_1$ and $E_2$, independently of one another, are each a group of the formula If or Ig

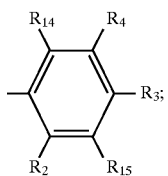
(If)

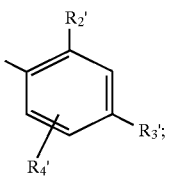
(Ig)

and in which

A is —C(=O)—CR$_5$=CH—R$_6$;

R$_1$, independently of one another, are —CH$_2$—CH(XA)—CH$_2$—O—R$_7$, —CR$_8$R'$_8$—(CH$_2$)$_l$—XA, —CH$_2$—CH(OA)—R$_9$,

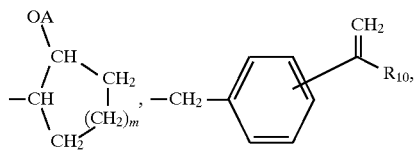

—CH$_2$—C(=CH$_2$)—R$_{10}$, —(CH$_2$)$_p$—SiR$_{11}$R$_{11}$'—CH=CH$_2$, —C(=O)—(CH$_2$)$_q$—CH=CH$_2$, —CHR$_8$—(CH$_2$)$_r$—C(=O)—O—CH$_2$—CH(OH)—CH$_2$—OA, —CR$_8$R'$_8$—(CH$_2$)$_l$—C(=O)—XA or —C(=O)—O—CH$_2$—C(=CH$_2$)—R$_{10}$; and, in the case where E$_1$ is a group of the formula If in which neither of the radicals R$_2$ and R$_{14}$ is hydrogen, R$_1$ can additionally be —A or —CH$_2$—CH(OH)—CH$_2$—XA;

R$_2$, independently of one another, are H, C$_1$–C$_{12}$alkyl, C$_5$–C$_{12}$cycloalkyl, C$_3$–C$_6$alkenyl, halogen, phenyl or trifluoromethyl;

R$_2$', independently of one another, are C$_1$–C$_{18}$alkoxy, C$_2$–C$_{18}$alkenoxy, —OH or —O—COR$_2$;

R$_3$ and R$_3$', independently of one another, are H, —OH, —OR$_1$, —OR$_{131}$, C$_1$–C$_{18}$alkyl, C$_3$–C$_{18}$alkenyl, C$_6$–C$_{12}$cycloalkyl, halogen, trifluoromethyl, phenyl, phenyl-C$_1$–C$_4$alkyl, —CN, C$_1$–C$_{18}$alkyl-S(=O)$_t$— or phenyl-S(=O)$_t$—;

R$_4$, R$_4$' and R$_4$", independently of one another, are H, C$_1$–C$_{18}$alkyl, C$_3$–C$_6$alkenyl —OR$_{131}$, halogen, trifluoromethyl, phenyl, phenyl-C$_1$–C$_4$alkyl, mono- to tri-C$_1$–C$_4$alkyl-substituted phenyl-C$_1$–C$_4$alkyl, —CN, C$_1$–C$_{18}$alkyl-S(=O)$_t$— or phenyl-S(=O)$_t$—;

R$_5$ is H, —CH$_2$—COOR$_{13}$, C$_1$–C$_4$alkyl or —CN; R$_6$ is H, —COOR$_{13}$, C$_1$–C$_{17}$alkyl or phenyl;

R$_7$ is C$_1$–C$_{18}$alkyl, C$_5$–C$_{12}$cycloalkyl, C$_3$–C$_{18}$alkenyl; phenyl which is substituted by one to three C$_1$–C$_8$alkyl, C$_1$–C$_8$alkoxy, C$_3$–C$_8$alkenoxy, halogen or trifluoromethyl radicals;

phenyl-C$_1$–C$_4$alkyl; C$_3$–C$_{50}$alkyl which is interrupted by one or more —O—; 1-adamantyl;

2-adamantyl, norbornyl, 2-methylnorbornyl, —C(=O)—R$_{12}$ or —A;

R$_8$ and R$_8$', independently of one another, are H, C$_1$–C$_{18}$alkyl, phenyl, phenyl-C$_1$–C$_4$alkyl, or phenyl substituted by 1–3 C$_1$–C$_8$alkyl, C$_1$–C$_8$alkoxy, C$_3$–C$_8$alkenoxy, halogen, CF$_3$;

R$_9$ is C$_1$–C$_{18}$alkyl, phenyl or phenyl-C$_1$–C$_4$alkyl; R$_{10}$ is H or —CH$_3$;

R$_{11}$ and R$_{11}$', independently of one another, are C$_1$–C$_4$alkyl or phenyl or phenyl which is substituted by one to three C$_1$–C$_8$alkyl, C$_1$–C$_8$alkoxy, C$_3$–C$_8$alkenoxy, halogen or trifluoromethyl radicals;

R$_{12}$ is H, C$_1$–C$_{18}$alkyl, phenyl, phenyl-C$_1$–C$_4$alkyl, C$_5$–C$_{12}$cycloalkyl, C$_1$–C$_{12}$alkoxy, phenoxy, norborn-2-yl, 5-norbornen-2-yl or 1-adamantyl;

R$_{13}$ is H, C$_1$–C$_{18}$alkyl, C$_3$–C$_{18}$alkenyl, phenyl, C$_5$–C$_{12}$cycloalkyl, C$_3$–C$_{50}$alkyl which is interrupted by one or more —O—, phenyl which is substituted by one to three C$_1$–C$_8$alkyl, C$_1$–C$_8$alkoxy, C$_3$–C$_8$alkenoxy, halogen or trifluoromethyl radicals, phenyl-C$_1$–C$_4$alkyl, 2-adamantyl, norbornyl or 2-methylnorbornyl;

R$_{14}$ and R$_{15}$, independently of one another, are H, C$_1$–C$_{18}$alkyl, C$_3$–C$_{18}$alkenyl, C$_6$–C$_{12}$cycloalkyl, halogen, CF$_3$, phenyl, phenyl-C$_1$–C$_4$alkyl, CN, C$_1$–C$_{18}$alkyl-S(=O)$_t$—, phenyl-S(=O)$_t$— or —OR$_{131}$;

R$_{131}$ is C$_1$–C$_{18}$alkyl, C$_1$–C$_{18}$alkyl which is substituted by OH, C$_1$–C$_{18}$alkoxy, C$_5$–C$_{12}$cycloalkoxy, C$_3$–C$_6$alkenyloxy, halogen, —COOR$_{13}$, —CONH$_2$, —COHNR$_{132}$, —CON(R$_{132}$)(R$_{133}$), —NHCOR$_{12}$, —CN, —OCOR$_{12}$, phenoxy and/or by phenoxy which is substituted by C$_1$–C$_{18}$alkyl, C$_1$–C$_{18}$alkoxy or halogen, or is C$_3$–C$_{18}$alkenyl, C$_6$–C$_{12}$cycloalkyl, C$_1$–C$_4$alkyl and/or —OCOR$_{12}$-substituted C$_6$–C$_{12}$cycloalkyl; C$_3$–C$_{50}$alkyl which is interrupted by one or more —O— and may be substituted by OH or —O—COR$_{12}$;

phenyl, phenyl-C$_1$–C$_4$alkyl, —COR$_{12}$ or —SO$_2$R$_{12}$;

R$_{132}$ and R$_{133}$, independently of one another, are C$_1$–C$_{12}$alkyl, C$_3$–C$_{12}$alkoxyalkyl, C$_4$–C$_{16}$dialkylaminoalkyl or C$_5$–C$_{12}$cycloalkyl; or R$_{132}$ and R$_{133}$ together are C$_3$–C$_9$alkylene, C$_3$–C$_9$oxaalkylene or -azaalkylene;

X is —NR$_8$—, —O—, —NH—(C$_n$H$_{2n}$)—NH— or —O—(C$_k$H$_{2k}$)—NH—;

k is a number from 2 to 4;

l is a number from 0 to 9;

m is a number from 2 to 8;

n is a number from 0 to 4;

p is a number from 0 to 10;

q is a number from 1 to 8;

r is a number from 0 to 18; and t is the number 0, 1 or 2.

Corresponding polymers regarded below as UV absorbers of the formula (Id).

Examples of said radicals are given above under the compounds of the formula (I).

Among the polymeric UV absorbers of formula Id are those compounds a subject of special interest which are obtainable by polymerization of compounds of formula Id, wherein R$_1$ is

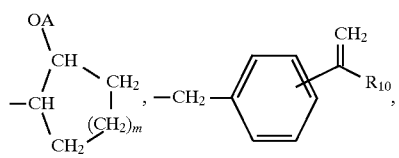

—CH$_2$—C(=CH$_2$)—R$_{10}$, —(CH$_2$)$_p$—SiR$_{11}$R$_{11}$'—CH=CH$_2$, —C(=O)—(CH$_2$)$_q$—CH=CH$_2$, —CHR$_8$—(CH$_2$)$_r$—C(=O)—O—CH$_2$—CH(OH)—CH$_2$—OA, —CR$_8$R'$_8$—(CH$_2$)$_1$—C(=O)—XA or —C(=O)—O—CH$_2$—C(=CH$_2$)—R$_{10}$, and, if E$_1$ or E$_1$ and E$_2$ are a group of formula Ig (compounds derived from bis(2-hydroxyphenyl)triazine or tris(2-hydroxyphenyl)triazine), R$_1$ also embraces —CH$_2$—CH(XA)—CH$_2$—O—R$_7$, —CR$_8$R'$_8$—(CH$_2$)$_1$—XA, —CH$_2$—CH(OA)—R$_9$, —CH$_2$—CH(OH)—CH$_2$—XA; and, in the case where E$_1$ is a group of the formula If in which neither of the radicals R$_2$ and R$_{14}$ is hydrogen, R$_1$ also embraces —CH$_2$—CH(XA)—CH$_2$—O—R$_7$, —CR$_8$R'$_8$—(CH$_2$)$_1$—XA, —CH$_2$—CH(OA)—R$_9$, —CH$_2$—CH(OH)—CH$_2$—XA or —A;

especially those, wherein R$_1$ is

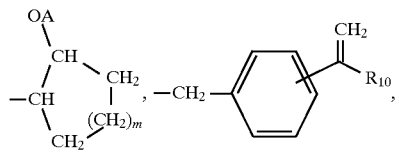

—(CH$_2$)$_p$—SiR$_{11}$R$_{11}$'—CH=CH$_2$, —CHR$_8$—(CH$_2$)$_r$—C(=O)—O—CH$_2$—CH(OH)—CH$_2$—OA, —CR$_8$R'$_8$—(CH$_2$)$_1$—C(=O)—XA or —C(=O)—O—CH$_2$—C(=CH$_2$)—R$_{10}$, and, if E$_1$ or E$_1$ and E$_2$ are a group of formula Ig, R$_1$ additionally embraces —CH$_2$—C(=CH$_2$)—R$_{10}$, —C(=O)—(CH$_2$)$_q$—CH=CH$_2$, —CH$_2$—CH(XA)—CH$_2$—O—R$_7$, —CR$_8$R'$_8$—(CH$_2$)$_1$—XA, —CH$_2$—CH(OA)—R$_9$, —CH$_2$—CH(OH)—CH$_2$—XA; and, in the case where E$_1$ is a group of the formula If in which neither of the radicals R$_2$ and R$_{14}$ is hydrogen, R$_1$ also embraces —CH$_2$—CH(XA)—CH$_2$—O—R$_7$, —CR$_8$R'$_8$—(CH$_2$)$_1$—XA, —CH$_2$—CH(OA)—R$_9$, —CH$_2$—CH(OH)—CH$_2$—XA or —A.

A group of compounds especially preferred among these are compounds, wherein E$_1$ is a group of formula If and E$_2$ is a group of formula Ig (compounds derived from bis(2-hydroxyphenyl)triazine).

Novel polymeric compounds are obtainable for example, by addition polymerization of at least one compound of the formula (Ih) or at least one compound of the formula (Ih) and at least one further ethylenically unsaturated compound

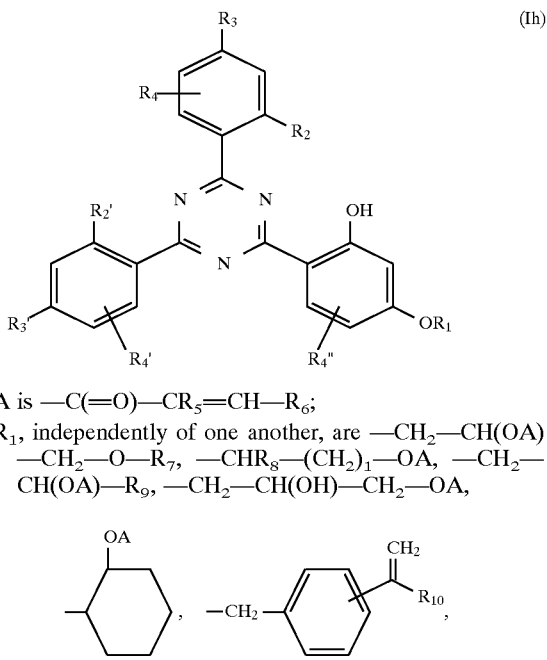

A is —C(=O)—CR$_5$=CH—R$_6$;

R$_1$, independently of one another, are —CH$_2$—CH(OA)—CH$_2$—O—R$_7$, —CHR$_8$—(CH$_2$)$_1$—OA, —CH$_2$—CH(OA)—R$_9$, —CH$_2$—CH(OH)—CH$_2$—OA, —CH$_2$—C(=CH$_2$)—R$_{10}$, —(CH$_2$)$_p$—SiR$_{11}$R$_{11}$'—CH=CH$_2$, —C(=O)—(CH$_2$)$_q$—CH=CH$_2$, —CHR$_8$—(CH$_2$)$_r$—C(=O)—O—CH$_2$—CH(OH)—CH$_2$—OA or —C(=O)—O—CH$_2$—C(=CH$_2$)—R$_{10}$;

R$_2$ and R$_2$', independently of one another, are H, —OH, —OA, C$_1$–C$_{12}$alkyl, cyclohexyl, C$_3$–C$_6$alkenyl, C$_1$–C$_{18}$alkoxy, C$_2$–C$_{18}$alkenoxy, halogen, phenyl or trifluoromethyl;

R$_3$ and R$_3$', independently of one another, are H, —OH, —OA, —OR$_1$, C$_1$–C$_{12}$alkyl, cyclohexyl, C$_3$–C$_6$alkenyl, C$_1$–C$_{18}$alkoxy, C$_3$–C$_{18}$alkenoxy, halogen, trifluoromethyl, phenyl, phenoxy, phenyl-C$_1$–C$_4$alkyl, phenyl-C$_1$–C$_4$alkoxy, —CN, C$_1$–C$_{18}$galkyl-S(=O)$_t$— or phenyl-S(=O)$_t$—;

R$_4$, R$_4$' and R$_4$'', independently of one another, are H, C$_1$–C$_{12}$alkyl, C$_3$–C$_6$alkenyl, C$_1$–C$_{18}$alkoxy, C$_3$–C$_{18}$alkenoxy, halogen, trifluoromethyl, phenyl, phenoxy, phenyl-C$_1$–C$_4$alkyl, mono- to tri-C$_1$–C$_4$alkyl-substituted phenyl-C$_1$–C$_4$alkyl, phenyl-C$_1$–C$_4$alkoxy, —CN, C$_1$–C$_{18}$alkyl-S(=O)$_t$— or phenyl-S(=O)$_t$—;

R$_5$ is H, —CH$_2$—COOR$_{13}$, C$_1$–C$_4$alkyl or —CN;

R$_6$ is H, —COOR$_{13}$, C$_1$–C$_{17}$alkyl or phenyl;

R$_7$ is C$_1$–C$_{18}$alkyl, cyclohexyl, C$_3$–C$_{18}$alkenyl, phenyl, phenyl which is substituted by one to three C$_1$–C$_8$alkyl, C$_1$–C$_8$alkoxy, C$_3$–C$_8$alkenoxy, halogen or trifluoromethyl radicals, phenyl-C$_1$–C$_4$alkyl or —C(=O)—R$_{12}$;

R$_8$ is H or C$_1$–C$_{18}$alkyl;

R$_9$ is C$_1$–C$_{18}$alkyl, phenyl or phenyl-C$_1$–C$_4$alkyl;

R$_{10}$ is H or —CH$_3$;

R$_{11}$ and R$_{11}$', independently of one another, are C$_1$–C$_4$alkyl or phenyl or phenyl which is substituted by one to three C$_1$–C$_8$alkyl, C$_1$–C$_8$alkoxy, C$_3$–C$_8$alkenoxy, halogen or trifluoromethyl radicals;

R$_{12}$ is C$_1$–C$_{18}$alkyl, C$_2$–C$_{18}$alkenyl or phenyl;

R$_{13}$ is H, C$_1$–C$_{18}$alkyl, C$_3$–C$_{18}$alkenyl or phenyl;

l is a number from 0 to 19;

p is a number from 0 to 10;
q is a number from 1 to 8;
r is a number from 0 to 18; and
t is the number 0, 1 or 2.

Preferred meanings of the radicals in the formula Id are given below:

$R_1$ is preferably —$CH_2$—CH(XA)—$CH_2$—O—$R_7$, —$CR_8R'_8$—$(CH_2)_1$—XA, —$CH_2$—CH(OA)—$R_9$,

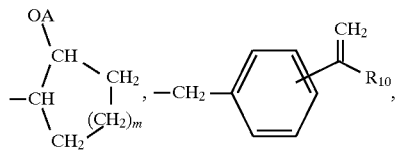

—$CHR_8$—$(CH_2)_r$—C(=O)—O—$CH_2$—CH(OH)—$CH_2$—OA; particularly preferably —$CH_2$—CH(OA)—$CH_2$—O—$R_7$, —$CHR_8$—$(CH_2)_1$—OA, —$CH_2$—CH(OA)—$R_9$,

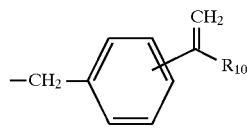

or —$CHR_8$—$(CH_2)_r$—C(=O)—O—$CH_2$—CH(OH)—$CH_2$—OA; and very particularly preferably —$CH_2$—CH(OA)—$CH_2$—O—$R_7$, —$CHR_8$—$(CH_2)_1$—OA, —$CH_2$—CH(OA)—$R_9$ or

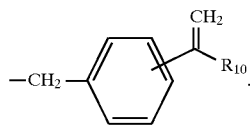

$R_2$ is preferably H, $C_1$–$C_4$alkyl, $C_3$alkenyl, F, Cl or phenyl; particularly preferably H, —$CH_3$ or Cl; and very particularly preferably H or —$CH_3$.

$R_2'$ is preferably —OH, $C_1$–$C_4$alkoxy or $C_3$alkenoxy; particularly preferably $C_1$–$C_2$alkoxy or —OH.

$R_3$ and $R_3'$ are preferably H, —OH, —$OR_1$, —$OR_{131}$, $C_1$–$C_4$alkyl, cyclohexyl, $C_3$alkenyl, F, Cl, trifluoromethyl, phenyl, benzyl or —CN; particularly preferably H, —OH, —$OR_1$, —$CH_3$, $C_1$–$C_{12}$alkoxy, $C_2$–$C_6$alkanoyloxy-substituted $C_2$–$C_{18}$alkoxy, $C_3$alkenoxy, F, Cl, phenyl, benzoxy or —CN; and very particularly preferably H, —OH, —$OR_1$, —$CH_3$, $C_1$–$C_{12}$alkoxy, Cl, phenyl or —CN.

$R_3'$ is frequently —OH, —OR, or —$OR_{131}$, and $R_3$ does not include the meaning —$OR_1$.

$R_4$, $R_4'$ and $R_4''$ are preferably, H, $C_1$–$C_4$alkyl, $C_3$alkenyl, $C_1$–$C_4$alkoxy, $C_3$alkenoxy, F, Cl, trifluoromethyl, phenyl, phenyl-$C_1$–$C_3$alkyl or —CN; particularly preferably H, —$CH_3$, $C_3$alkenyl, —$OCH_3$, $C_3$alkenoxy, F, Cl, phenyl-$C_3$alkyl or —CN; and very particularly preferably H or —$CH_3$.

$R_5$ is preferably H or —$CH_3$.

$R_6$ is preferably H, —$COOR_{13}$, —$CH_3$ or phenyl; and particularly preferably H or —$CH_3$.

$R_7$ is preferably $C_1$–$C_8$alkyl, cyclohexyl, $C_3$–$C_8$alkenyl, phenyl, phenyl which is substituted by one to three $C_1$–$C_4$alkyl or $C_1$–$C_4$alkoxy radicals or benzyl, and particularly preferably $C_1$–$C_8$alkyl, cyclohexyl, $C_3$alkenyl, phenyl or benzyl.

$R_8$ and $R_8'$ are preferably, independently of one another, H or $C_1$–$C_8$alkyl.

$R_{10}$ is preferably hydrogen.

$R_{11}$ and $R_{11}'$, independently of one another, are preferably $C_1$–$C_4$alkyl or phenyl, especially methyl.

X is preferably —O— or —$NR_8$—, particularly an oxygen atom.

The value of the index l is preferably 1–15.

Preference is given to compounds of the formula (Id), in which $R_1$, independently of one another, are —$CH_2$—CH(XA)—$CH_2$—O—$R_7$, —$CR_8R_8'$—$(CH_2)_1$—XA,

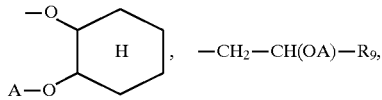, —$CH_2$—CH(OA)—$R_9$,

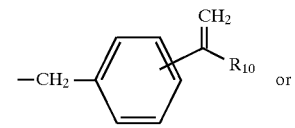 or

—$CHR_8$—$(CH_2)_r$—C(=O)—O—$CH_2$—CH(OH)—$CH_2$—OA;

$R_2$ is H, $C_1$–$C_4$ alkyl, $C_3$alkenyl, F, Cl or phenyl;

$R_2'$ is $C_1$–$C_4$alkoxy, $C_3$alkenoxy, —OA, —O—$COR_{12}$ or —OH;

$R_3$ and $R_3'$, independently of one another, are H, —OH, —$OR_1$, —$OR_{131}$, $C_1$–$C_4$alkyl, cyclohexyl, $C_3$alkenyl, F, Cl, trifluoromethyl, phenyl, benzyl or —CN;

$R_4'$ and $R_4''$, independently of one another, are H, $C_1$–$C_4$alkyl, $C_3$alkenyl, $C_1$–$C_4$alkoxy, $C_3$alkenoxy, F, Cl, trifluoromethyl, phenyl, phenyl-$C_1$–$C_3$alkyl or —CN;

$R_5$ is H or —$CH_3$;

$R_6$ is H, —$COOR_{13}$, —$CH_3$ or phenyl;

$R_7$ is $C_1$–$C_8$alkyl, cyclohexyl, $C_3$–$C_8$alkenyl, phenyl, phenyl which is substituted by one to three $C_1$–$C_4$alkyl or $C_1$–$C_4$alkoxy radicals, or benzyl;

$R_8$ and $R_8'$, independently of one another, are H or $C_1$–$C_{18}$alkyl;

$R_9$ is $C_1$–$C_{10}$alkyl, phenyl or benzyl;

$R_{12}$ is H, $C_1$–$C_{18}$alkyl, phenyl, phenyl-$C_1$–$C_4$alkyl or cyclohexyl;

$R_{13}$ is $C_1$–$C_4$alkyl, $C_3$alkenyl, cyclohexyl, phenyl-$C_1$–$C_4$alkyl or phenyl;

$R_4$, $R_{14}$ and $R_{15}$, independently of one another, are H, F, Cl, $C_1$–$C_4$alkoxy, $CF_3$, phenyl, CN or $C_1$–$C_8$alkyl;

$R_{131}$ is $C_1$–$C_{18}$alkyl, $C_3$–$C_{18}$alkyl which is substituted by OH, $C_1$–$C_{18}$alkoxy, $C_5$–$C_{12}$cycloalkoxy, —$COOR_{13}$, —$CONH_2$, —$COHNR_{132}$, —$CON(R_{132})(R_{133})$, —$NHCOR_{12}$, —CN, —$OCOR_{12}$ and/or phenoxy, or is $C_3$alkenyl, $C_6$–$C_{12}$cycloalkyl; $C_3$–$C_{50}$alkyl which is interrupted by one or more —O— and may be substituted by OH or O—$COR_{12}$; phenyl, phenyl-$C_1$–$C_4$alkyl, —$COR_{12}$ or —$SO_2R_{12}$;

X is —O— or —$NR_8$—;

l is a number from 1 to 19; and r is a number from 0 to 10.

Particular preference is given to polymers comprising units of the formula Id in which A is —C(=O)—$CR_5$=CH—$R_6$;

$R_1$, independently of one another, are —$CH_2$—CH(OA)—$CH_2$—O—$R_7$, —$CH_2$—CH(OA)—$R_9$,

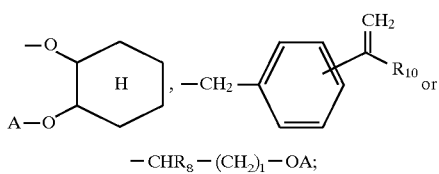

—CHR$_8$—(CH$_2$)$_l$—OA;

R$_2$ is H, —CH$_3$, —OCH$_3$, C$_3$alkenoxy or Cl;

R$_2$' is —OH;

R$_3$ is H, —CH$_3$, C$_1$–C$_4$alkoxy, C$_3$alkenoxy, F, Cl, phenyl, benzoxy or —CN;

R$_3$' is —OR$_1$ or —OR$_{131}$;

R$_4$, R$_{14}$ and R$_{15}$, independently of one another, are H, F, Cl, Phenyl, CH, OCH$_3$ or CH$_3$;

R$_4$' and R$_4$", independently of one another, are H, —CH$_3$, C$_3$alkenyl, —OCH$_3$, C$_3$alkenoxy, F, Cl, phenyl-C$_3$alkyl or —CN;

R$_5$ is H or —CH$_3$;

R$_6$ is H or —CH$_3$;

R$_7$ is C$_1$–C$_8$alkyl, cyclopentyl, cyclohexyl, C$_3$alkenyl, phenyl or benzyl;

R$_8$ is H or C$_1$–C$_{18}$alkyl;

R$_9$ is C$_1$–C$_{10}$alkyl or phenyl;

R$_{12}$ is C$_1$–C$_{18}$alkyl, phenyl or cyclohexyl;

R$_{131}$ is C$_3$–C$_{18}$alkyl or C$_3$–C$_{18}$alkyl which is substituted by C$_1$–C$_{18}$alkoxy, OH, phenoxy, —NHCOR$_{12}$ and/or —OCOR$_{12}$; and l is a number from 1 to 19;

very particularly those in which

A is —C(=O)—CR$_5$=CH—R$_6$;

R$_1$, independently of one another, are —CH$_2$—CH(OA)—CH$_2$—O—R$_7$, —CH$_2$—CH(OA)—R$_9$,

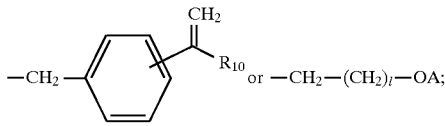

R$_2$ is H or CH$_3$;

R$_2$' is —OH;

R$_3$ is H, —CH$_3$, Cl or phenyl;

R$_3$' is —OR$_1$ or —OR$_{131}$;

R$_4$ is H or CH$_3$;

R$_4$', R$_4$", R$_{14}$ and R$_{15}$ are hydrogen;

R$_5$ is H or —CH$_3$;

R$_6$ is H;

R$_7$ is C$_1$–C$_8$alkyl;

R$_9$ is C$_1$–C$_{10}$alkyl;

R$_{12}$ is C$_1$–C$_8$alkyl;

R$_{131}$ is C$_3$–C$_{18}$alkyl or C$_3$–C$_{18}$alkyl which is substituted by —OCOR$_{12}$; and l is a number from 1 to 10.

Especial preference is given to compounds of the formula (Id) in which at least one of the radicals R$_3$ and R$_3$' is —OR$_1$.

The invention furthermore relates, particularly interestingly, to novel polymers comprising units of the formula Id in which E$_1$ conforms to the formula If and E$_2$ conforms to the formula Ig. Of these, particular preference is given to compounds with mixed substituents in which neither R$_3$ nor R$_3$' is —OR$_1$; especially those in which R$_2$' is OH and R$_3$' is C$_1$–C$_{18}$alkoxy or C$_2$–C$_{18}$alkoxy which is interrupted by —O— or by —OCOR$_{12}$ and/or is substituted by C$_1$–C$_{18}$alkoxy or C$_5$–C$_{12}$cycloalkoxy, where R$_{12}$ is C$_1$–C$_{18}$alkyl, phenyl, phenyl-C$_1$–C$_4$alkyl or C$_5$–C$_{12}$cycloalkyl especially those compounds in which R$_1$ is —CR$_8$R$_8$'—(CH$_2$)$_l$—XA.

Both homopolymers and copolymers are suitable, where the copolymers can be built up from at least two different compounds (structural units) of the formula (Id) or at least one compound of the formula (Id) and one further comonomer (ethylenically unsaturated compound). The compounds of the formula I can likewise be employed for the preparation of the novel homopolymers as well as copolymers.

There is also particular technical interest in polymeric compounds obtainable by copolymerization of at least two different compounds of the formula (Id).

Suitable further comonomers (comonomers which are different from compounds of the formula (Id)) include acrylic acid, methacrylic acid, acrylates, methacrylates, acrylamides, methacrylamides, vinyl ethers, styrene, styrene derivatives, vinylpyridines, acrylonitrile, methacrylonitrile, vinylpyrrolidone, derivatives of vinylpyrrolidone, and ethylenically unsaturated derivatives of sterically hindered amines, 2-(2'-hydroxyphenyl)benzotriazoles, 2-hydroxybenzophenones and sterically hindered phenols.

Particular importance is attached to the use of other copolymerizable stabilizers, for example ethylenically unsaturated derivatives of sterically hindered amines (HALS), 2-(2'-hydroxyphenyl)benzotriazoles, 2-hydroxybenzophenones or sterically hindered phenols.

In copolymers which, in addition to units of at least one compound of the formula Id, also contain further comonomers and which can be employed as light stabilizers, the further comonomer:monomer of the formula Id ratio is preferably up to 10:1, in particular in the range from 1:1 to 5:1.

Corresponding HALS which can be used as comonomer are generally characterized by the structural unit

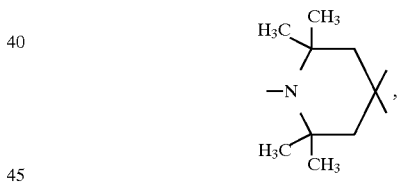

where the 3 free bonds are saturated by H or an organic substituent, and the molecule contains at least one polymerizable, ethylenically unsaturated double bond; corresponding compounds are described, inter alia, in U.S. Pat. No. 4,942,238, U.S. Pat. No. 4,983,737 and EP-A-0 634 399, and the literature cited therein.

Corresponding 2-(2'-hydroxyphenyl)benzotriazoles which can be used as comonomer are generally characterized by the structural unit

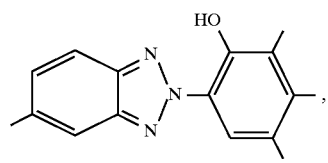

where the four free bonds are saturated by H or organic substituents, and the molecule contains at least one polymerizable, ethylenically unsaturated double bond; corresponding compounds are described, inter alia, in U.S. Pat.

No. 5,099,027, U.S. Pat. No. 4,528,311, U.S. Pat. No. 5,147,902, Research Disclosure 32, 592, U.S. Pat. No. 4,785,063, U.S. Pat. No. 4,892,915, U.S. Pat. No. 4,611,061, EP-A-0 190 003, EP-A-0 508 744, U.S. Pat. No. 4,716,234, U.S. Pat. No. 3,493,539, U.S. Pat. No. 5,234,807, U.S. Pat. No. 5,256,359, U.S. Pat. No. 5,385,815, U.S. Pat. No. 5,372,922, JP-A-03-139 590, EP-A-0 431 868, JP-A-03-8547, GB-A-2 232 667, EP-A-0 282 294, EP-A-0 343 996, EP-A-0 133 164, EP-A-0 131 468, J. Macromol. Sci., Pure Appl. Chem. A30 (9–10), 741 (1993) and Polym. Bull. 12 (5), 375 (1984), and the literature cited therein.

Corresponding 2-hydroxybenzophenones which can be used as comonomer are generally characterized by the structural unit

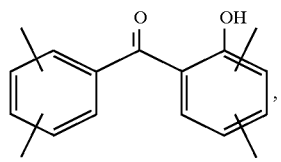

where the four free bonds are saturated by H or organic substituents, and the molecule contains at least one polymerizable, ethylenically unsaturated double bond; corresponding compounds are described, inter alia, in CH-B-383 001 and CH-B-376 899, and the literature cited therein.

Corresponding sterically hindered phenols which can be used as comonomer are generally characterized by the structural unit

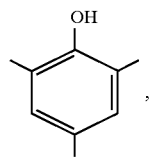

where the three free bonds are saturated by organic substituents, and the molecule contains at least one polymerizable, ethylenically unsaturated double bond, usually in the substituent in the p-position to the hydroxyl group; corresponding compounds are described, inter alia, in U.S. Pat. No. 3,708,520 and the literature cited therein.

The further comonomers (comonomers which are different from compounds of the formula (Id)) are preferably compounds of the formulae (II)–(VII) below

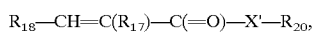

in which

X' is —O— or —NR$_{19}$—;

R$_{17}$ is H, C$_1$–C$_4$alkyl, —CH$_2$—COOR$_{21}$, —Cl or —CN;

R$_{18}$ is H, —COOR$_{21}$ or —CH$_3$;

R$_{19}$ is H, C$_1$–C$_8$alkyl, C$_4$–C$_{12}$cycloalkyl, —N(R$_x$)$_2$-substituted C$_1$–C$_4$alkyl, —S(=O)—R$_x$, —C(CH$_3$)$_2$—CH$_2$—C(=O)—CH$_3$, —C(CH$_3$)$_2$—CH$_2$—SO$_3$M, —(CH$_2$)$_s$—SO$_3$M or

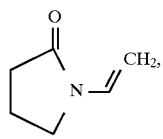

R$_{20}$ is H, C$_1$–C$_{18}$alkyl, C$_2$–C$_{18}$alkenyl, C$_2$–C$_{18}$alkyl which is interrupted by one or more O atoms and can be substituted by OH, or —(CH$_2$)$_s$—SO$_3$M,

—CH$_2$F, —CH$_2$Cl, —CH$_2$CN, —CH$_2$CH$_2$Cl, —CH$_2$CH$_2$CN, —CH$_2$CH$_2$—COOR$_x$, C$_7$–C$_{11}$phenylalkyl, naphthyl, —N(R$_x$)$_2$-substituted C$_1$–C$_4$alkyl, adamantyl or C$_6$–C$_{12}$cycloalkyl;

R$_{21}$ is H, C$_1$–C$_{18}$alkyl, phenyl or C$_2$–C$_{18}$alkenyl;

R$_x$ is C$_1$–C$_4$alkyl or phenyl;

R$_Y$ is H, C$_1$–C$_{12}$alkyl, phenyl, —CO—OR$_x$, —CN, —F, or —Cl;

M is H or an alkali metal; and s is a number from 1 to 5.

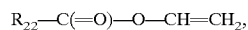

in which R$_{22}$ is C$_1$–C$_{19}$alkyl or phenyl.

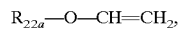

in which R$_{22a}$ is C$_1$–C$_{18}$alkyl.

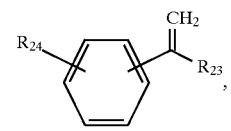

in which R$_{23}$ is H or —CH$_3$;

R$_{24}$ is H, —CR$_{23}$=CH$_2$, —C(O)—phenyl or —SO$_3$M; and

M is H or an alkali metal.

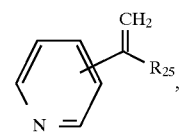

in which R$_{25}$ is H or —CH$_3$.

in which R$_{26}$ is H, —F, —Cl or —CH$_3$ and R$_{27}$ is —Cl, —Br, —F or —CN.

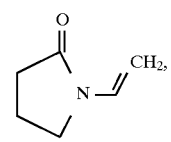

and the abovementioned polymerizable, ethylenically unsaturated derivatives of sterically hindered amines (HALS), 2-(2'-hydroxyphenyl)benzotriazoles, 2-hydroxybenzophenones and sterically hindered phenols.

Preferred comonomers of the formulae (I)–(VII) are:

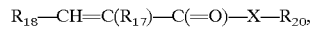

in which R$_{17}$ is H, —CH$_3$, —CH$_2$—COOR$_{21}$ or —CN;

R$_{18}$ is H, —COOR$_{21}$ or —CH$_3$;

R$_{19}$ is H, C$_1$–C$_4$alkyl, —C(CH$_3$)$_2$—CH$_2$—C(=O)—CH$_3$, —C(CH$_3$)$_2$—CH$_2$—SO$_3$M or —(CH$_2$)$_s$—SO$_3$M;

$R_{20}$ is H, $C_1$-$C_{18}$alkyl, $C_2$-$C_{30}$alkyl which is interrupted by one or more O atoms, or —$(CH_2)_s$—$SO_3M$;

$R_{21}$ is H, $C_1$-$C_{18}$alkyl, phenyl or $C_2$-$C_{18}$alkenyl;

M is H or an alkali metal;

X is —O— or —$NR_{19}$—; and s is a number from 1 to 5.

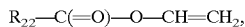  (III)

in which $R_{22}$ is $C_1$-$C_{19}$alkyl or phenyl.

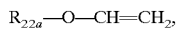  (IIIa)

in which $R_{22a}$ is $C_1$-$C_8$alkyl.

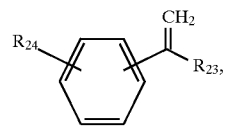  (IV)

in which $R_{23}$ is H or —$CH_3$;

$R_{24}$ is H, —$CR_{23}$=$CH_2$, —C(O)-phenyl or —$SO_3M$; and

M is H or an alkali metal.

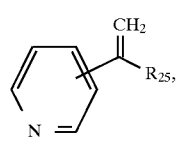  (V)

in which $R_{25}$ is H or —$CH_3$.

  (VI)

in which $R_{26}$ is H or $CH_3$.

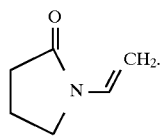  (VII)

The possible meanings of the substituents in the formulae (II)–(VII) correspond to those as given above for the compounds of the formula (I) and (Id).

Any substituents in the above formulae which are alkyl having up to 18 carbon atoms which is interrupted by one or more O atoms are radicals such as —$(CH_2$—$CH_2$—$O)_{1-8}$—$CH_3$, —$(CH_2$—$CH_2$—$O)_{1-8}$—$C_2H_5$ or —$(CH_2$—$CH_2$—$CH_2O)_{1-5}$—$CH_3$.

Any substituents in the above formulae which are alkali metal are Li, Na or K.

Particularly preferred further comonomers (comonomers which are different from compounds of the formula (Id)) are compounds of the formulae (II)–(IV) and (VII).

Preference is given to copolymers obtainable by polymerization of at least one preferred compound of the formula (Id) and at least one of the comonomers of the formulae (II)–(VII).

Particular preference is given to copolymers obtainable by polymerization of at least one particularly preferred compound of the formula (Id) and at least one of the comonomers of the formulae (II)–(IV) or (VII).

Very particular preference is given to copolymers obtainable by polymerization of at least one very particularly preferred compound of the formula (Id) and at least one of the comonomers of the formulae (II)–(IV) or (VII), where $R_{17}$ is H or —$CH_3$;

$R_{18}$ is H or —$CH_3$;

$R_{19}$ is H, $C_1$-$C_4$alkyl, —$C(CH_3)_2$—$CH_2$—$SO_3M$ or —$(CH_2)_s$—$SO_3M$;

$R_{20}$ is H, $C_1$-$C_8$alkyl, or $C_2$-$C_{20}$alkyl which is interrupted by one or more O atoms;

$R_{22}$ is —$CH_3$;

$R_{22a}$ is $C_1$-$C_4$alkyl;

$R_{23}$ and $R_{24}$ are H;

M is H, Li, Na or K;

X is —O— or —$NR_{19}$—; and s is the number 2 or 3.

The compounds of the formula (I) or (Id) are known or can be prepared by methods known in principle. The reaction schemes below show a fundamental two-step (a+b) process for the preparation of compounds of the formula (I) or (Id) derived from triazinylmonoresorcinols. Compounds derived from bis- or trisresorcinol can also be prepared analogously. Further details on possible preparation processes are given in EP-A-0 434 608.

a) Alkylation of the para-OH group of the resorcinol radical (by, for example, a glycidyl ether or an ω-bromoalcohol):

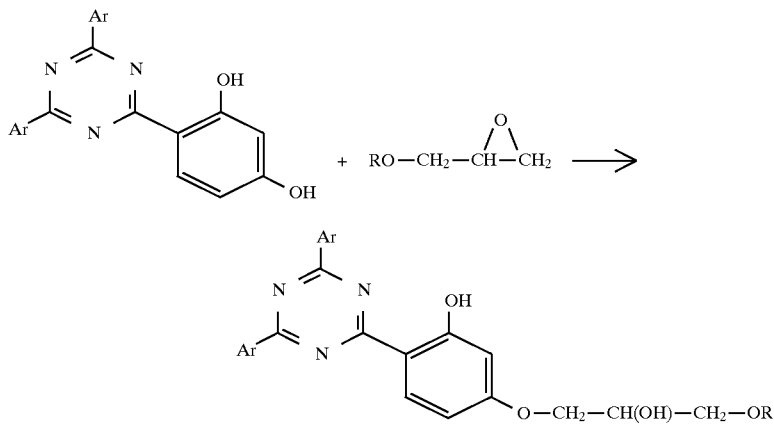

(Ar = substituted or unsubstituted phenyl; R = e.g. alkyl)

-continued
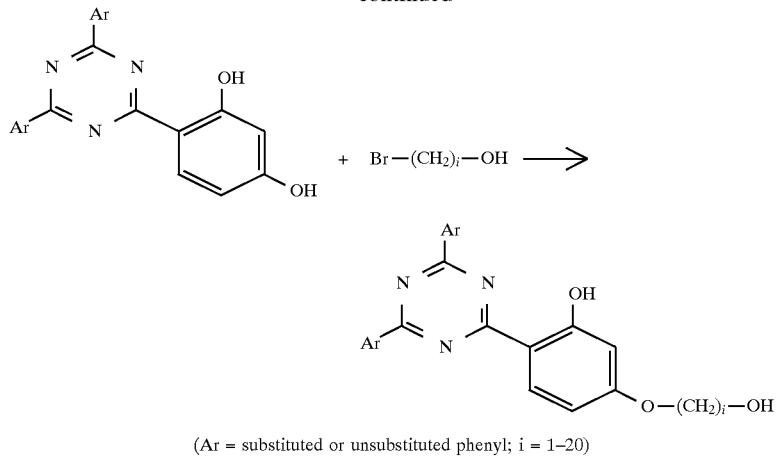
(Ar = substituted or unsubstituted phenyl; i = 1–20)
b) Acrylation or methacrylation of the aliphatic OH group:
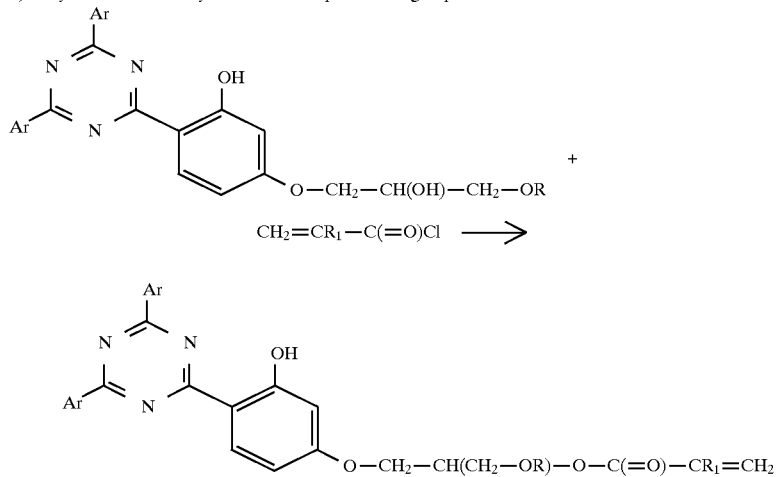
(Ar = substituted or unsubstituted phenyl; R = e.g. alkyl; $R_1$ = H or $-CH_3$)
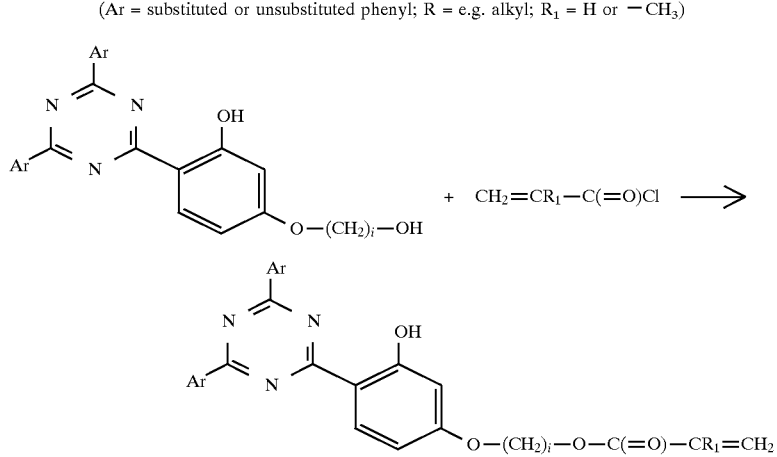
(Ar = substituted or unsubstituted phenyl; i: 1–20; $R_1$ = H or $-CH_3$)

The triazinylresorcinols of the formula

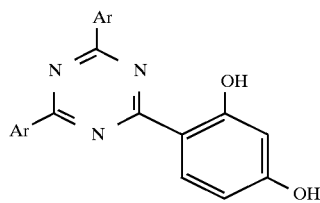

used as starting compounds can likewise be prepared by known methods or analogously thereto (EP-A-0 434 608; H. Brunetti and C. E. Lüthi, Helv. Chim. Acta 55, 1566 (1972); EP-A-0 577 559; GB-A-884 802).

The polymerization (addition polymerization) of one of the monomeric compounds of the formula (Id) can be initiated by free-radical, anionic or cationic initiators. Preference is given to free-radical initiators, which decompose to form free radicals on warming, for example organic peroxides or hydroperoxides, azo compounds or redox catalysts. The polymerization can also be initiated by high-energy radiation. The polymerization can be carried out in solution, emulsion, dispersion or in bulk. These processes are known to the person skilled in the art Suitable polymerization processes are also described in EP-A-0 577 122, page 9, line 46 to page 10, line 35.

Examples of compounds of the formula (I) are the following:

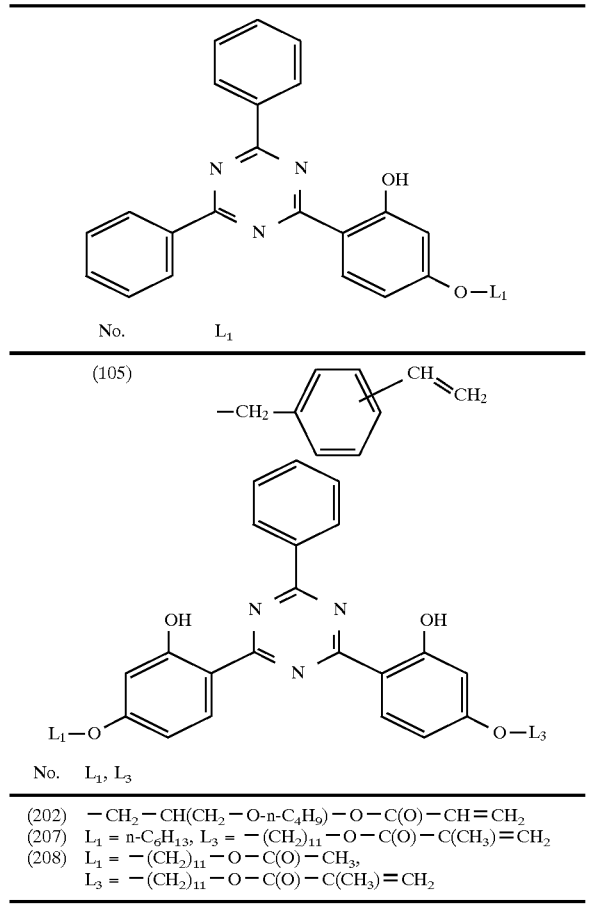

| No. | $L_1$ |
|---|---|
| (105) | —CH$_2$—C$_6$H$_4$—CH=CH$_2$ |

| No. | $L_1$, $L_3$ |
|---|---|
| (202) | —CH$_2$—CH(CH$_2$—O-n-C$_4$H$_9$)—O—C(O)—CH=CH$_2$ |
| (207) | $L_1$ = n-C$_6$H$_{13}$, $L_3$ = —(CH$_2$)$_{11}$—O—C(O)—C(CH$_3$)=CH$_2$ |
| (208) | $L_1$ = —(CH$_2$)$_{11}$—O—C(O)—CH$_3$, $L_3$ = —(CH$_2$)$_{11}$—O—C(O)—C(CH$_3$)=CH$_2$ |

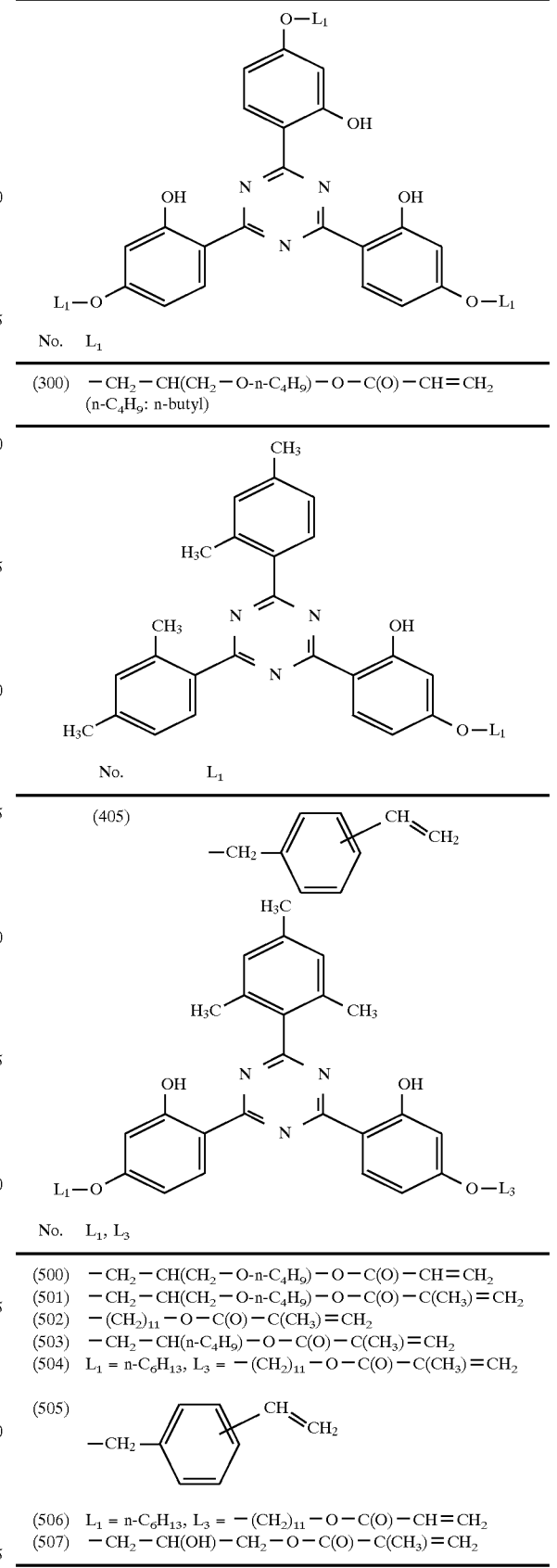

| No. | $L_1$ |
|---|---|
| (300) | —CH$_2$—CH(CH$_2$—O-n-C$_4$H$_9$)—O—C(O)—CH=CH$_2$ (n-C$_4$H$_9$: n-butyl) |

| No. | $L_1$ |
|---|---|
| (405) | —CH$_2$—C$_6$H$_4$—CH=CH$_2$ |

| No. | $L_1$, $L_3$ |
|---|---|
| (500) | —CH$_2$—CH(CH$_2$—O-n-C$_4$H$_9$)—O—C(O)—CH=CH$_2$ |
| (501) | —CH$_2$—CH(CH$_2$—O-n-C$_4$H$_9$)—O—C(O)—C(CH$_3$)=CH$_2$ |
| (502) | —(CH$_2$)$_{11}$—O—C(O)—C(CH$_3$)=CH$_2$ |
| (503) | —CH$_2$—CH(n-C$_4$H$_9$)—O—C(O)—C(CH$_3$)=CH$_2$ |
| (504) | $L_1$ = n-C$_6$H$_{13}$, $L_3$ = —(CH$_2$)$_{11}$—O—C(O)—C(CH$_3$)=CH$_2$ |
| (505) | —CH$_2$—C$_6$H$_4$—CH=CH$_2$ |
| (506) | $L_1$ = n-C$_6$H$_{13}$, $L_3$ = —(CH$_2$)$_{11}$—O—C(O)—CH=CH$_2$ |
| (507) | —CH$_2$—CH(OH)—CH$_2$—O—C(O)—C(CH$_3$)=CH$_2$ |

Examples of monomers of the formula (Id), besides those mentioned above, are the following compounds:

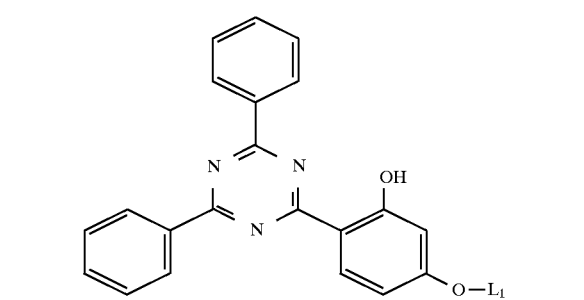

| No. | L$_1$ |
|---|---|
| (100) | $-CH_2-CH(CH_2-O\text{-n-}C_4H_9)-O-C(O)-CH=CH_2$ (n-C$_4$H$_9$: n-butyl) |
| (101) | $-CH_2-CH(CH_2-O\text{-n-}C_4H_9)-O-C(O)-C(CH_3)=CH_2$ |
| (102) | $-(CH_2)_{11}-O-C(O)-CH=CH_2$ |
| (103) | $-(CH_2)_{11}-O-C(O)-C(CH_3)=CH_2$ |
| (104) | $-CH_2-CH(\text{n-}C_4H_9)-O-C(O)-C(CH_3)=CH_2$ |
| (106) | $-CH_2-CH_2-O-C(O)-C(CH_3)=CH_2$ |

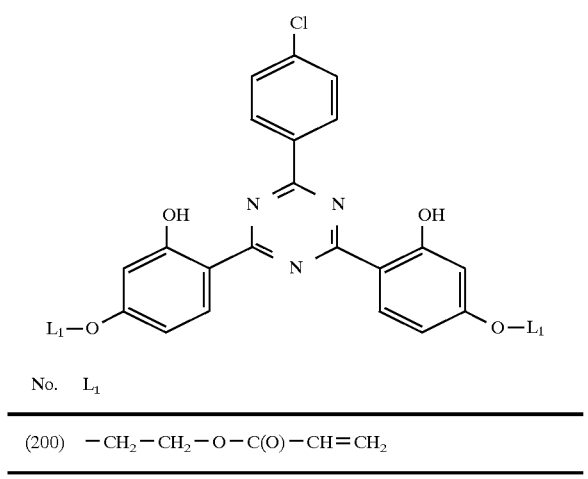

| No. | L$_1$ |
|---|---|
| (200) | $-CH_2-CH_2-O-C(O)-CH=CH_2$ |

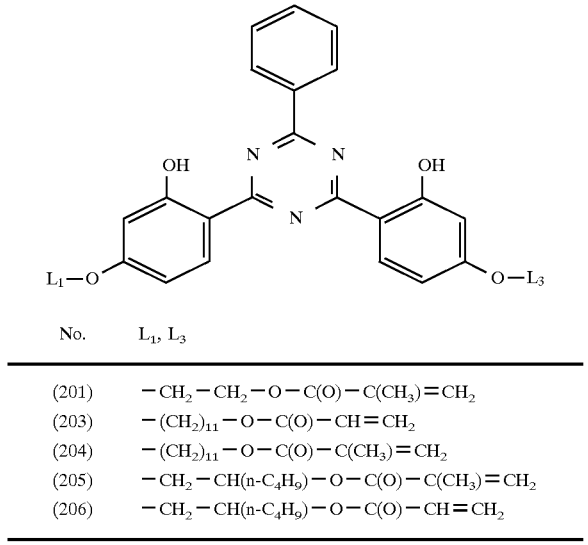

| No. | L$_1$, L$_3$ |
|---|---|
| (201) | $-CH_2-CH_2-O-C(O)-C(CH_3)=CH_2$ |
| (203) | $-(CH_2)_{11}-O-C(O)-CH=CH_2$ |
| (204) | $-(CH_2)_{11}-O-C(O)-C(CH_3)=CH_2$ |
| (205) | $-CH_2-CH(\text{n-}C_4H_9)-O-C(O)-C(CH_3)=CH_2$ |
| (206) | $-CH_2-CH(\text{n-}C_4H_9)-O-C(O)-CH=CH_2$ |

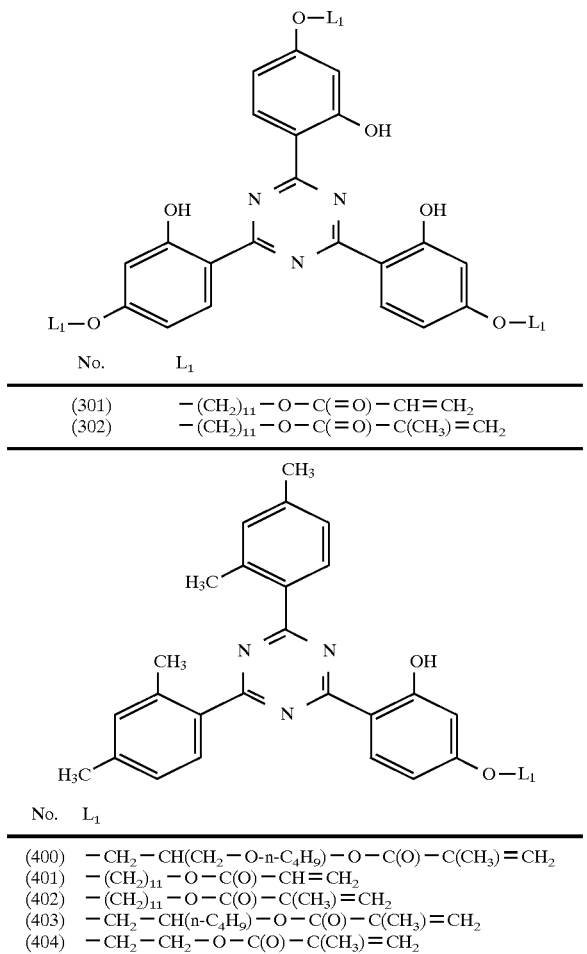

| No. | L$_1$ |
|---|---|
| (301) | $-(CH_2)_{11}-O-C(=O)-CH=CH_2$ |
| (302) | $-(CH_2)_{11}-O-C(=O)-C(CH_3)=CH_2$ |

| No. | L$_1$ |
|---|---|
| (400) | $-CH_2-CH(CH_2-O\text{-n-}C_4H_9)-O-C(O)-C(CH_3)=CH_2$ |
| (401) | $-(CH_2)_{11}-O-C(O)-CH=CH_2$ |
| (402) | $-(CH_2)_{11}-O-C(O)-C(CH_3)=CH_2$ |
| (403) | $-CH_2-CH(\text{n-}C_4H_9)-O-C(O)-C(CH_3)=CH_2$ |
| (404) | $-CH_2-CH_2-O-C(O)-C(CH_3)=CH_2$ |

Examples of polymers made from compounds of the formula (Id) are the following:
(600) homopolymer of compound (204)
(601) copolymer of compound (204) and n-butyl acrylate in the molar ratio 1:4
(602) homopolymer of compound (207)
(603) copolymer of compound (207) and n-butyl acrylate in the molar ratio 1:4
(604) homopolymer of compound (504)
(605) copolymer of compound (504) and n-butyl acrylate in the molar ratio 1:4
(606) copolymer of compound (504) and n-dodecyl methacrylate in the molar ratio 1:4
(607) homopolymer of compound (102)
(608) copolymer of compound (102) and n-butyl acrylate in the molar ratio 1:4
(609) homopolymer of compound (402)
(610) copolymer of compound (402) and n-butyl acrylate in the molar ratio 1:2
(611) homopolymer of compound (103)
(612) copolymer of compound (103) and n-butyl acrylate in the molar ratio 1:2
(613) homopolymer of compound (400)
(614) copolymer of compound (400) and n-butyl acrylate in the molar ratio 1:2
(615) copolymer of compound (105) and n-butyl acrylate in the molar ratio 1:2
(616) copolymer of compound (405) and n-butyl acrylate in the molar ratio 1:2.

In addition to the novel copolymers mentioned above, compounds of the formula (I) can also be incorporated by copolymerization into polymers prepared by polymerization of ethylenically unsaturated monomers. These include, for example, the following monomers: acrylic acid, methacrylic acid, esters of acrylic and methacrylic acid, amides of acrylic and methacrylic acid, acrylonitrile, styrene, α-methylstyrene, butadiene, isoprene, maleic anhydride, esters, amides and imides of maleic acid, vinyl chloride, vinylidene chloride, vinyl acetate, vinylbutyral, vinyl alkyl ethers and N-vinylpyrrolidone. Preference is given to incorporation into polymers built up from acrylic acid, methacrylic acid, esters or amides of acrylic or methacrylic acid, styrene or acrylonitrile. The polymer can be built up from one or more of such monomers. The addition of the unsaturated compound of the formula (I) is carried out during the polymerization, so that copolymerization takes place.

The polymerization can be initiated by free-radical, anionic or cationic initiators. Preference is given to free-radical initiators which decompose on warming to form free radicals, for example organic peroxides or hydroperoxides, azo compounds or redox catalysts. The polymerization can also be initiated by high-energy radiation, for example in radiation-curable surface coatings (UV-curable or ESR-curable). In this case, the copolymerizable hydroxyphenyl-s-triazine is incorporated into the coating matrix during film formation.

A particularly suitable process for such copolymerizations is group-transfer polymerization, in which a "living" polymer is formed by using certain initiators. Examples of initiators which are suitable for this purpose are 1-trimethylsiloxy-1-alkoxy-2-methylpropenes. The group-transfer polymerization process has been known for some years and is described, for example, in U.S. Pat. No. 4,695,607 and U.S. Pat. No. 4,414,372.

The polymerization can be carried out in solution, emulsion, dispersion or in bulk. These processes are known to the person skilled in the art.

Suitable compounds of the formula (I) for incorporation by copolycondensation or copolyaddition are in particular those which contain two functional groups. If only small amounts of a compound of the formula (I) are to be incorporated by polycondensation or polyaddition, suitable compounds of the formula (I) are also those containing only one functional group.

Monofunctional, difunctional or trifunctional compounds of the formula (I) can be incorporated, for example, into polyesters, polyether esters, polyamides, polyurethanes, polycarbonates, epoxy resins, phenolic resins, melamine resins or alkyd resins. The incorporation is carried out by addition during preparation of the condensation or addition polymers by methods known for this purpose to the person skilled in the art.

The incorporation can also take place into oligomeric or polymeric intermediates. For example, unsaturated compounds of the formula (I) can be added to unsaturated polyester resins and mixtures thereof with other vinyl compounds, and the mixture is then cured with addition of free-radical initiators. Alternatively, oligomeric epoxy resins can be reacted with functional compounds of the formula (I) and the products subsequently cured using an epoxide curing agent. Furthermore, OH-functional compounds of the formula (I) can be reacted with melamine resins, and the resultant compounds subsequently cured with addition of acrylate resins.

Incorporation is also possible into polyurethanes, phenolic resins or alkyd resins using a precursor before final curing of the resin. The curing of the resin can also take place with acidic or basic catalysis without affecting the triazine compounds.

A further incorporation possibility comprises reacting a compound of the formula (I) with a polymer containing suitable functional groups. These can be, for example, polymers containing hydroxyl, carboxyl, anhydride, amino, epoxide or isocyanate groups. Examples thereof are copolymers of acrylic and methacrylic acid, of hydroxyalkyl (meth) acrylates, of glycidyl (meth)acrylates, partially hydrolyzed polyvinyl acetate or ethylene-vinyl acetate copolymer, partially esterified cellulose, partially hydrolyzed polyalkyl (meth)acrylates, polyesters or polyurethanes containing reactive terminal groups, epoxy resins or copolymers of maleic acid, maleic anhydride or maleic acid monoesters or monoamides.

Compounds of the formula (I) which are suitable for the reaction are those which contain a functional group which can react with the functional groups of the polymers. These can be, for example, hydroxyl, carboxyl, ester, amino, epoxide or isocyanate groups. If it is desired, for example, to modify a polymer containing OH groups by means of a compound of the formula (I), use can be made, for example, of a compound of the formula (I) containing at least one isocyanate, epoxide, carboxyl or ester group. A polymer containing epoxide groups can be reacted, for example, with a compound of the formula (I) containing at least one hydroxyl, carboxyl or amino group. A copolymer of maleic anhydride can be reacted, for example, with a compound of the formula (I) containing a hydroxyl, amino or epoxide group.

These reactions are carried out by generally conventional methods for polymer-homologous reactions. The reaction is preferably carried out in solution. It is possible to react all the functional groups of the polymer or only some thereof. This depends on the amount of compound of the formula (I) used for the reaction. The examples below give details of such reactions.

A specific method of incorporation into polymers is grafting of ethylenically unsaturated derivatives of the formula (I) onto hydrocarbon polymers. The compounds of the formula (I) containing ethylenically unsaturated groups have already been defined in greater detail.

Hydrocarbon polymers can be saturated or unsaturated. The former include polyolefins, for example polyethylene, polypropylene, polybutene and polyisobutene. The latter include diene polymers and copolymers thereof with olefins, for example polybutadiene, polyisoprene, propylene-butadiene and ethylene-propylene-butadiene. Preference is given to grafting onto polyolefins, in particular onto polyethylene.

The grafting reaction can be carried out in solution or in bulk. The catalysts used are free-radical formers, as also used for the homopolymerization or copolymerization of the unsaturated compounds.

All these processes for incorporating compounds of the formula (I) into polymers can be carried out using a relatively small amount of the triazine, for example using from 0.05 to 5% by weight, based on the modified polymer. These amounts give the polymer resistance to damage by light, oxygen and heat, and this stabilization cannot be lost due to migration or elution of the stabilizer. For this purpose, it is preferred to incorporate from 0.1 to 3% by weight of a compound of the formula (I).

However, this process can also be used to incorporate larger amounts of the triazine, for example from 5 to 50% by weight, based on the modified polymer. This is appropriate if it is desired to use the polymers modified in this way as polymeric stabilizers. These polymeric stabilizers can be added to organic materials, in particular organic polymers. However, the polymeric stabilizers can also be applied to plastic mouldings as a thin protective coating, for example in dissolved form or by coextrusion, as described, for example, in U.S. Pat. No. 4,676,870.

A further application of this process is the incorporation of compounds of the formula (I) into polymer microparticles. EP-A-0 226 538 describes the incorporation of light stabilizers by copolyaddition or copolycondensation into microparticles which can be used as the disperse phase in coatings. In this case, from 0.1 to 30% by weight, preferably from 0.5 to 10% by weight, based on the modified polymer, of a compound of the formula (I) are incorporated into the microparticles.

The incorporation into microparticles can advantageously be carried out using the group-transfer polymerization process, as described, for example, in EP-A-0 293 871.

The invention also relates to the modified polymers prepared by the outlined process which contain a compound of the formula (I) in chemically bonded form in the stated amounts by weight and which are thus stabilized against damage by light, oxygen and heat.

The novel stabilizers of the formula I and of the formula Id and the polymers modified in accordance with the invention can be mixed with various additives, as is conventional in polymer technology. These additives can be stabilizers or processing auxiliaries or pigments or other additives. Examples thereof are the following additives:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-do-decylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dim-ethyl-4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1 -bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)-amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonate acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]-octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo-[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl) trimethylenediamine, N,N'-bis(3,5-di-tert-butyl-4-hydroxyphenylpropionyl)hydrazine.

1.18. Ascorbic acid (vitamin C)

1.19. Aminic antioxidants, for example N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)-diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylamino-phenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, bis[4-(1',3'-dimethylbutyl) phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octylphenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethyl-piperid-4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotiazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl )-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl) phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyl-oxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylene-bis[4-(,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$—]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl (α-cyano-β-methyl-p-methoxy-cinnamate, methyl α-carbomethoxy-p- methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis( 1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triaza-spiro[4.5]decan-2,4-dion, bis(1-octyloxy-2,2,6,6-tetramethylpiperidyl) sebacate, bis( 1-octyloxy-2,2,6,6-tetramethylpiperidyl) succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl) pyrrolidine-2,5-dione, a mixture of 4-hexadecyloxyand 4-stearyloxy-2,2,6,6-tetramethylpiperidine, a condensation product of N,N'-bis-(2,2,6,6-tetramethyl-4-piperidyl) hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl- 1-oxa-3,8-diaza-4-oxo-spiro[4,5]decane, a reaction product of 7,7,9,9-tetramethyl-2-cyclo-undecyl-1-oxa-3,8-diaza-4-oxospiro [4,5]decane und epichlorohydrin.

2.7. Oxamides, for example 4,4'-dioctyloxyoxanilide, 2,2'-diethoxyoxanilide, 2,2'-dioc-tyloxy-5,5'-di-tert-butoxanilide, 2,2'-didodecyloxy-5,5'-di-tert-butoxanilide, 2-ethoxy-2'-ethylanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)- 1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)- 1,3,5-triazine, 2-[2-hydroxy-4-(2-hydroxy-3-butyloxy-propoxy) phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(saticyloyl)oxalyl dihydrazide, N,N'-bis(salicyloyl) thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]- 1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methylphosphite, bis(2,4-di-tert-butyl-6-methylphenyl) ethylphosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridecyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers ("ionomers").

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4 316 611, DE-A-4 316 622, DE-A-4 316 876, EP-A-0 589 839 or EP-A-0 591 102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]-phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

Of particular importance is the addition of sterically hindered amines (Section 2.6 in the above list), since these give particularly effective light stabilization with the modified polymers.

If the additives are stabilizers, they are preferably added in a total amount of from 0.05 to 5% by weight.

In a further embodiment of the invention, a further stabilizer is incorporated into the polymer in addition to a compound of the formula (I). Of particular interest is the additional incorporation of a sterically hindered amine. Depending on whether use is made of a sterically hindered amine containing an ethylenically unsaturated group or another functional group, the incorporation can take place by copolycondensation or copolyaddition or by reaction with a polymer containing suitable functional groups.

Sterically hindered amines which contain ethylenically unsaturated groups and are suitable in accordance with the invention for copolymerization are, for example, the acrylic and methacrylic acid derivatives of 2,2,6,6-tetramethylpiperidine described in U.S. Pat. No. 3,705,166, and the N-alkyl and N-alkoxy derivatives thereof. Further copolymerizable derivatives of tetramethylpiperidine are described in U.S. Pat. No. 4,210,612 and in EP-A-0 389 420.

Examples of sterically hindered amines which can react with functional polymers are those containing hydroxyl groups, for example 2,2,6,6-tetramethyl-4-piperidinol, 1,2,2,6,6-pentamethyl-4-piperidinol, 1-hydroxyethyl-2,2,6,6-tetramethyl-4-piperidinol and the compounds described in U.S. Pat. No. 4,087,404 and in EP-A-0 389 419; or those containing amino groups, for example 4-amino-2,2,6,6-tetramethylpiperidine or the 4-aminopiperidines described in U.S. Pat. No. 3,904,581.

The incorporation of these sterically hindered amines can take place before, at the same time as or after the incorporation of the triazines of the formula (I). The processes used for this purpose are the same as for the incorporation of the triazines. Further details are given in the examples below.

If, in addition to the triazine compound of the formula (I), a sterically hindered amine is also incorporated into the polymer, the latter is preferably used in an amount which corresponds to from 0.1 to 15% by weight of the modified polymer. The same applies to a novel copolymer comprising units of the formula Id.

The polymers modified in accordance with the invention can be used for conventional use forms of polymers, for example as mouldings, tubes, sheets, films, fibres, casting resins, adhesives or coatings. They are preferably used as binders for surface coatings (both pigmented and unpigmented).

The compounds of the formula (I) or (Id) and the modified polymers can furthermore, as stated above, be used as stabilizers for organic materials, predominantly for polymers. To this end, the modified polymers used are preferably those containing at least 5%, for example 5–50%, of a compound of the formula (I) or (Id) in incorporated form. The novel stabilizers are preferably used in an amount of from 0.01 to 10% by weight, in particular from 0.5 to 5% by weight (based on the organic material to be stabilized). The novel compounds can be used for stabilizing organic materials, for example oils, fats, waxes, cosmetics, paints or coatings, in particular for stabilizing organic polymers. Examples of polymers which can be stabilized in this way are the following:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups Ivb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (–Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoLefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly((α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/ styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile butadiene copolymers, acrylonitrile/alkyl acrylate copolymers, acrylonitrile/alkoxyalkyl acrylate or acrylonitrile/vinyl halide copolymers or acrylonitrile alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in I) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

The invention therefore also relates to a process for stabilizing organic material against damage by light, oxygen and/or heat, which comprise adding thereto, as stabilizer, a compound of the formula (I) or a polymer built up from monomers of the formula (Id) and, if desired, further monomers, and to the use of these compounds for stabilizing organic material.

The amount of stabilizer to be used depends on the organic material to be stabilized and on the intended use of the stabilized material. In general, the novel composition contains, per 100 parts by weight of material to be stabilized, from 0.01 to 15 parts by weight, in particular from 0.05 to 10 parts by weight, especially from 0.1 to 5 parts by weight, of the stabilizer.

The incorporation into the organic polymers, for example into the synthetic organic, in particular thermoplastic polymers, can take place by addition of the novel compounds and, if desired, further additives by the conventional methods in the art. The incorporation can expediently take place before or during shaping, for example by mixing the pulverulent components or by addition of the stabilizer to the melt or solution of the polymer, or by application of the dissolved or dispersed compounds to the polymer, if necessary with subsequent evaporation of the solvent. In the case of elastomers, these can also be stabilized as lattices. A further way of incorporating the novel compounds into polymers comprises adding them before or during the polymerization of the corresponding monomers or before the crosslinking.

The novel compounds or mixtures thereof can also be added to the plastics to be stabilized in the form of a masterbatch containing these compounds in, for example, a concentration of from 2.5 to 25% by weight.

The incorporation of the novel compounds can expediently be carried out by the following methods:

as an emulsion or dispersion (for example into lattices or emulsion polymers)

as a dry mix during mixing of additional components or polymer mixtures by direct addition into the processing equipment (for example extruder, internal mixer, etc.)

as a solution or melt.

The stabilized polymer compositions obtained in this way can be converted-into shaped articles, for example fibres, films, tapes, sheets, sandwich boards, containers, tubes and other profiles, by conventional methods, for example by hot pressing, spinning, extrusion or injection moulding.

The invention therefore furthermore relates to the use of the novel polymer compositions for the production of shaped articles.

Also of interest is use in multilayer systems. In this case, a novel polymer composition having a relatively high content of stabilizer of the formula (I) or the polymer comprising monomers of the formula (Id) and, if desired, further monomers, for example 5–15% by weight, is applied in a thin film (10–100 $\mu$m) to a shaped article made from a polymer containing little or no stabilizer of the formula (I) or (Id). The application can be carried out at the same time as shaping of the article, for example by coextrusion. However, the application can also be carried out to the ready-shaped article, for example by lamination with a film or by coating with a solution. The outer layer or layers of the finished article have the function of a UV filter which protects the interior of the article against UV light. The outer layer preferably contains 5–15% by weight, in particular 5–10% by weight, of at least one stabilizer of the formula (I) or (Id).

The use of the novel polymer compositions for the production of multilayer systems in which the outer layer(s) in a thickness of 2–100 $\mu$m comprises a novel polymer composition, while the inner layer contains little or no stabilizer of the formula (I) or (Id) therefore represents a further subject-matter of the invention.

Of particular interest is the use of a novel polymer composition in which component A is a polycarbonate for the production of multilayer systems.

The polymers stabilized in this way are distinguished by high weathering resistance, in particular high resistance to UV light. They thus retain their mechanical properties and their colour and gloss, even when used outside for an extended period.

The stabilizer can also be a mixture of two or more novel compounds. The novel compositions, stabilized coating compositions or organic materials can also, in addition to the stabilizer of the formula (I) or (Id) also contain other stabilizers or other additives, for example antioxidants, further light stabilizers, metal deactivators, phosphites or phosphonites. Examples thereof are the antioxidants, light stabilizers and other additives (3.–11.) mentioned above.

The examples below describe the subject-matter of the invention in greater detail without representing a limitation. In the examples, parts are parts by weight and % are % by weight. If room temperature is mentioned in an example, this is taken to mean a temperature in the range from 20°–25° C. These definitions apply in each case unless otherwise stated. Numbers directly following chemical symbols denote indices of the chemical formula, even when not subscripted.

The following abbreviations apply:

| THF | tetrahydrofuran |
| --- | --- |
| AIBN | α,α'-azoisobutyronitrile |
| abs. | absolute (anhydrous) |
| m.p. | melting point or melting range |
| mmHg | Torr (1 mmHg = 133, 322 Pa) |
| MALDI | Matrix Assisted Laser Desorption Ionization |
| MS | mass spectrometry |
| NMR | nuclear magnetic resonance |
| GC | gas chromatography |
| GPC | gel permeation chromatography |
| DSC | differential scanning calorimetry |
| $M_n$ | number average molecular weight (unit g/mol) |
| $M_w$ | weight average molecular weight (unit g/Mol) |
| $T_g$ | glass transition temperature. |

EXAMPLE 1

Under nitrogen, a mixture of 14.2 g (30 mmol) of 2,4-diphenyl-6-[2-hydroxy-4-(3-n-butoxy-2-hydroxypropoxy) phenyl]-1,3,5-triazine, 3.5 g (38 mmol) of acryloyl chloride and 0.4 g (5 mmol) of pyridine in 100 ml of toluene is heated at 70° C. for 24 hours. 4.5 g (44 mmol) of triethylamine are added, and the mixture is heated at 70° C. for a further 6 hours. The mixture is allowed to cool, and the solid residue $((CH_3CH_2)_3N.HCl)$ is filtered off. The filtrate is evaporated, giving 17.5 g of the resin-like crude product. Column chromatography (silica gel 60; 230–400 mesh; eluent $CH_2Cl_2/CH_3OH$ 95/5) gives 12.5 g (79% yield) of 2,4-diphenyl-6-[2-hydroxy-4-(3-n-butoxy-2-acryloyloxypropoxy) phenyl]-1,3,5-triazine (compound 100) as a yellowish resin.

The $^1$H-NMR spectrum ($CDCl_3$, 300 MHz) is in agreement with the desired product.

Elemental analysis for $C_{31}H_{31}N_3O_5$(525.60): Theory: C:70.84 H:5.94 N:7.99% Found: C:70.80 H:5.85 N:8.02%

EXAMPLE 2

Under nitrogen, a mixture of 14.2 g (30 mmol) of 2,4-diphenyl-6-[2-hydroxy-4-(3-n-butoxy-2-hydroxypropoxy) phenyl]1,3,5-triazine, 8.0 g (76 mmol) of methacryloyl chloride and 0.4 g (5 mmol) of pyridine in 100 ml of toluene is heated at 80° C. for 48 hours. The excess methacryloyl chloride and the toluene are removed on a rotary evaporator. 100 ml of toluene and 4.5 g (44 mmol) of triethylamine are added, and the mixture is heated at 75° C. for 5 hours. The mixture is allowed to cool, and the solid residue $((CH_3CH_2)_3N.HCl)$ is filtered off. The filtrate is evaporated, giving 18.4 g of the crude product. Column chromatography (silica gel 60; 230–400 mesh; diameter 8 cm, h=30 cm; eluent $CH_2Cl_2$) gives 8.5 g of 2,4-diphenyl-6-[2-hydroxy-4-(3-n-butoxy-2-methacryloyloxypropoxy)phenyl]- 1,3,5-triazine (compound 101) as a yellowish resin.

The $^1$H-NMR spectrum ($CDCl_3$, 300 MHz) is in agreement with the desired product.

Elemental analysis for $C_{32}H_{33}N_3O_5$(539.63): Theory: C:71.22 H:6.16 N:7.79% Found: C:70.42 H:6.28 N:7.57%

Intermediate for Example 3

2-[2-Hydroxy-4-(11-hydroxy-undecyloxy)-phenyl]-4,6-diphenyl-1,3,5-triazine

The reaction is carried out under nitrogen protection.

A mixture of 170.7 g (0.5 mol) of 2-(2,4-dihydroxyphenyl)-4,6-diphenyl-1,3,5-triazine, 28.1 g (0.5 mol) of powdered potassium hydroxide (Fluka, >85%) in 1000 ml of diglyme (Fluka, 99%) is heated at 80° C. To this yellow solution are added 155.4 g (0.6 mol) of 11-bromo-1-undecanol (Fluka, 97%).

The mixture is heated at 100° C. for 40 hours.

The solid is filteried hot and the filtrate is cooled to 0° C.

The cristallised solid is filtered, washed with hexane and dried at 50° C./70 mmHg.

There is obtained 219.5 g (85.84% yield) of 2-[2-hydroxy-4-(11-hydroxy-undecyl-oxy)phenyl-]-4,6-diphenyl-1,3,5-triazine, as a pale yellow solid.

F. 131°–132° C.

Analysis: $C_{32}H_{37}N_3O_3$ Calc. C76.12 H7.29 N8.21 (511.67) Found C75.06 H7.46 N8.13

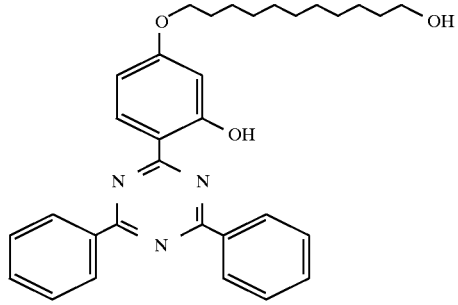

EXAMPLE 3

2-[2-Hydroxy-4-(11-acryloyl-oxy-undecyl-oxy)-phenyl-]-4,6-diphenyl-1,3,5-triazine The reaction is carried out under nitrogen protection.

To a mixture of 51.2 g (0.1 mol) of 2-[2-hydroxy-4-(11-hydroxy-undecyloxy-)-phenyl]-4,6-diphenyl)-1,3,5-triazine, 22.2 g (0.22 mol) of triethylamine, 500 ml of toluene (Merck, 99.5%), there is added dropwise 13.3 g (0.105 mol) of 3-chloropropionic acid chloride. Addition time:20 min. at 15° to 20° C. The mixture becomes a white suspension. The solid is filtered. Solvent is washed with water, dried with $Na_2SO_4$, and evaporated. The solid is filtered through a Kieselgel 60 pad, and eluted with toluene. There are obtained 44.8 g (79.2% yield) of 2-[2-hydroxy-4-(11-acryloyloxy-undecyloxy)phenyl]-4,6-diphenyl-1,3,5-triazine (compound No. 102) as a white solid. F. 123°–125° C.

Analysis: C35H39N3O4 Calc. C74.31 H6.95 N7.43 (565.71) Found C74.22 H7.08 N7.45

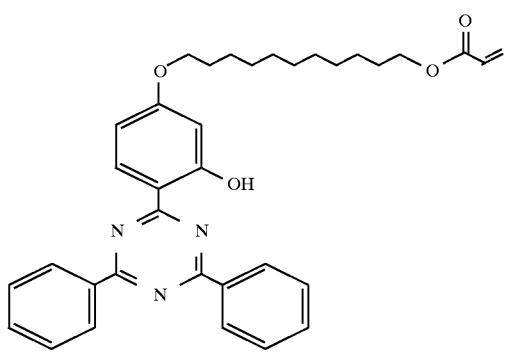

EXAMPLE 4

2-[2-Hydroxy-4-(1 1-methacryloyloxyundecyloxy) phenyl]-4,6-diphenyl-1,3,5-triazine The title compound (compound 103) is prepared by the method indicated in Example 3; melting point 94°–96° C.

EXAMPLE 4b

Mixture of 2-[2-Hydroxy-4-(3-vinylbenzoxy) phenyl-]-4,6-bis(2,4-dimethylphenyl)-1,3,5-triazine and 2-[2-Hydroxy-4-(4-vinylbenzoxy)phenyl-]-4,6-bis(2,4-dimethylphenyl)-1,3,5-triazine The title compound (compound 105) is prepared by the method indicated in Example 8b; melting point 158°–160° C.

EXAMPLE 4c

2-[2-Hydroxy-4-(2-methacryloyloxyethoxy)phenyl]-4,6-diphenyl-1,3,5-triazine

The title compound (compound 106) is obtained as a white solid by the method indicated in Example 3.

Analysis: $C_{27}H_{23}N_3O_4$ (453.50) Calculated: C71.57 H5.11 N9.27% Found: C70.70 H5.38 N9.00%

EXAMPLE 5

2,4-Bis(2,4-dimethylphenyl)-6-(2-hydroxy-4-(3-n-butoxy-2-methacryloyloxypropoxy)phenyl]-1,3,5-triazine The title compound (compound 400) of melting point 3° C. is obtained by the method indicated in Example 2. Intermediate for Example 6

2-[2-Hydroxy-4-(11-hydroxy-undecyloxy)-phenyl]-4,6-bis-(2,4-dimethylphenyl)-1,3,5-triazine The reaction is carried out under nitrogen protection.

A mixture of 79.5 g (0.2 mol) of 2-(2,4-dihydroxyphenyl)-4,6-(2,4-dimethylphenyl)1,3,5-triazine, 11.2 g (0.2 mol) of powdered potassium hydroxide (Fluka, >85%) in 500 ml of diglyme (Fluka, 99%) are heated at 80° C. To this yellow solution are added 59.6 g (0.23 mol) of 11-bromo-1-undecanol (Fluka, 97%). The mixture is heated at 100° C. for 46 hours. The solid is filtered hot and the filtrate is cooled to 0° C. The cristals are filtered, washed with hexane and dried at 50° C./70 mm. There are obtained 81.0 g (71.4% yield) of 2-[2-hydroxy-4-(11-hydroxyundecyloxy)phenyl]-4,6-bis-(2,4-dimethyl-phenyl)-1,3,5-triazine, as a pale yellow solid.

F. 95°–96° C.

Analysis: $C_{36}H_{45}N_3O_3$ Calc. C76.16 H7.99 N7.40 (567.78) Found C75.42 H7.92 N7.39

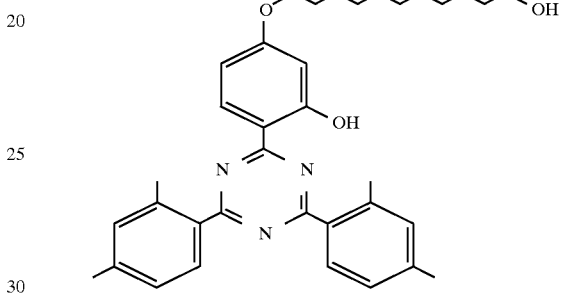

EXAMPLE 6

2-[2-Hydroxy-4-(11-acryloyloxy-undecyloxy) phenyl]-4,6-bis-(2,4-dimethylphenyl)-1,3,5-triazine (compound No. 401).

The reaction is carried out under nitrogen protection.

A mixture of 56.8 g (0.1 mol) of 2-[2-hydroxy-4-(11-hydroxy-undecyloxy)phenyl]-4,6-bis-(2,4-dimethylphenyl)-1,3,5-triazine, 12.4 g (0.133 mol) of acryloyl chloride (Fluka, 97%), 0.4 g of hydroquinone (Fluka, 98%), 2.0 ml of pyridine in 500 ml of toluene (Merck, 99.5%) are heated at 80° C. for 30 hours. The solution is cooled to 50° C., and 21.3 ml (0.154 mol) of triethylamine are added, followed by heating at 70° C. for 6 hours. The solid is filtered. Solvent is removed and the yellow solid is filtered through Kieselgel 60 pad, and eluted with toluene. The product is recrystallised in isopropanol. There are obtained 47.0 g (75.5% yield) of 2-[2-hydroxy-4-(11-acryloyloxyundecyloxy)phenyl]-2,4-bis-(2,4-dimethylphenyl)-1,3,5-triazine (compound No. 401) as a white solid; F. 81°–83° C.

Analysis: C39H47N3O4 Calc. C75.33 H7.62 N6.76 (621.82) Found C74.18 H7.75 N6.54

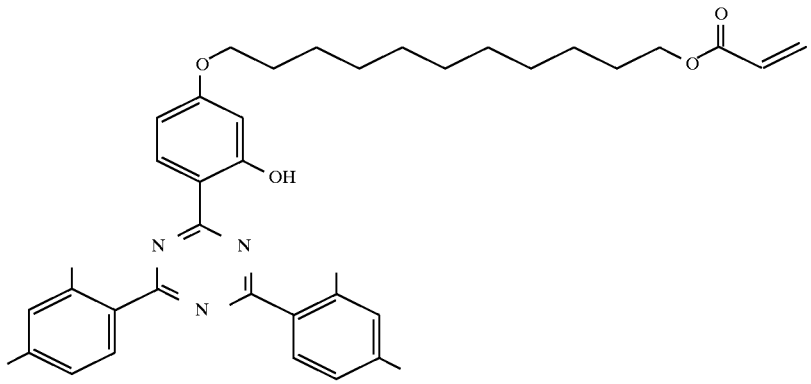

EXAMPLE 7

2,4-Bis(2,4-dimethylphenyl)-6-[2-hydroxy-4-(11-methacryloyloxyundecyloxy)-phenyl]-1,3,5triazine The title compound (compound 402) of melting point 71°–73° C. is obtained by the method indicated in Example 6.

EXAMPLE 8a 2,4-Bis(2,4-dimethylphenyl)-6-[2-hydroxy-4-(2-methacryloyloxyethoxy)phenyl]-1,3,5-triazine The title compound (compound 404) of melting point 132°–133° C. is obtained by the method indicated in Example 3.

EXAMPLE 8b

Mixture of 2-[2-hydroxy-4-(3vinylbenzoxy)-phenyl-]-4,6-bis-(2,4-dimethylphenyl)-1,3,5 -triazine and 2-[2-hydroxy-4-(4-vinylbenzoxy)-phenyl-]-4,6-bis-(2,4-dimethylphenyl)-1,3,5-triazine (compound 405).

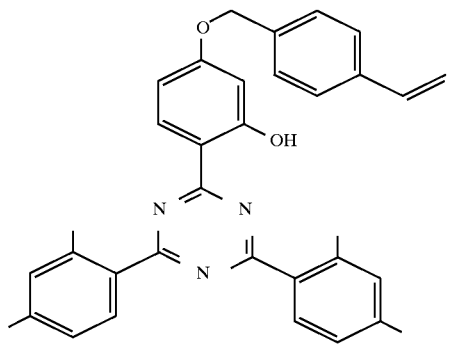

-continued

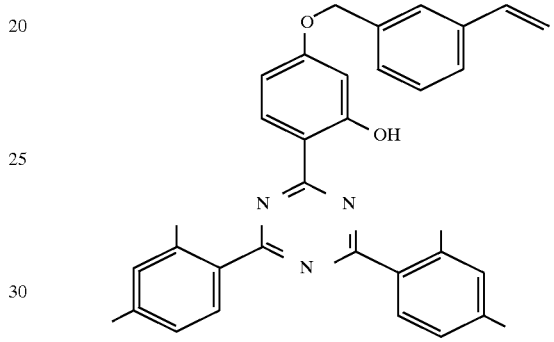

The reaction is carried out under nitrogen protection.

A mixture of 19.9 g (0.05 mol) of 2-[2,4-dihydroxyphenyl]-4,6-bis-(2,4-dimethylphenyl)-1,3,5-triazine, 8.4 g (0.055 mol) of vinylbenzyl chloride (Fluka, 98%; isomer mixture: 70% meta, 30% para), 3.1 g (0.055 mol) of potassium hydroxide and 100 ml of diglyme are heated at 110° C. for 3 hours. The suspension is cooled, 1 lt water is added, the solid is filtered and recrystallised in isopropanol. There are obtained 19.6 g (76.3% yield) of 2-[2-hydroxy-4-(3-/or4-vinylbenzoxy)-phenyl-]-2,4-bis-(2,4-dimethylphenyl)-1,3,5-triazine (compound No. 405) as a pale yellow solid; F. 110°–114° C.

Analysis: C34h31N3O2 Calc. C 79.51 H 6.08N 8.18 (513.64) Found C 79.53 H 5.98N 7.98

EXAMPLE 9

Under nitrogen, a mixture of 5.0 g (11 mmol) of 2-phenyl-4,6-bis[2-hydroxy-4-(2-hydroxyethoxy)phenyl]-1,3,5-triazine, 3.4 g (33 mmol) of methacryloyl chloride and 1.1 g (14 mmol) of pyridine in 35 ml of toluene is heated at 80° C. for 16 hours. The excess methacryloyl chloride and the toluene are removed at 60° C./60 mmHg. 40 ml of toluene and 3.8 g (38 mmol) of triethylamine are added, and the mixture is heated at 80° C. for 4 hours. The mixture is allowed to cool, and the solid residue is filtered off. Column chromatography (silica gel 60; 230–400 mesh; diameter 8 cm; h=30 cm; eluent toluene/ethyl acetate 1/1) gives 3.84 g of the crude product, which is recrystallized from 180 ml of ethyl acetate, giving 1.64 g of 2-phenyl-4,6-bis[2-hydroxy-4-(2-methacryloyloxyethoxy)phenyl]-1,3,5-triazine (compound 201) as a yellowish solid (melting point: 154°–159° C.).

The $^1$H-NMR spectrum (CDCl$_3$, 300 MHz) is in agreement with the desired product.

Elemental analysis for $C_{33}H_{31}N_3O_8$ (597.62): Theory: C: 66.32 H: 5.23N: 7.03% Found: C: 66.04 H: 5.37N: 7.03%

EXAMPLE 10

Under nitrogen, a mixture of 12.7 g (20 mmol) of 2-phenyl-4,6-bis[2-hydroxy-4-(3-n-butoxy-2-hydroxypropoxy)phenyl]-1,3,5-triazine, 4.3 g (46 mmol) of acryloyl chloride and 0.4 g (5 mmol) of pyridine in 80 ml of toluene is heated at 70° C. for 16 hours. After cooling to 50° C. and addition of 8.0 g (80 mmol) of triethylamine, the mixture is heated at 80° C. for 6 hours. The mixture is allowed to cool, and the solid residue (($CH_3CH_2)_3$N.HCl) is filtered off. The filtrate is evaporated, and the residue is then taken up in 200 ml of methylene chloride. The solution is filtered through a layer of silica gel (silica gel 60; 230–400 mesh), and washed with 450 ml of methylene chloride. Removal of the solvent and drying at 80° C. give 8.8 g (59% of theory) of 2-phenyl-4,6-bis[2-hydroxy-4-(3-n-butoxy-2-acryloyloxypropoxy)phenyl]-1,3,5-triazine (compound 202) as an orange resin.

The $^1$H-NMR spectrum ($CDCl_3$, 300 MHz) is in agreement with the desired product.

Elemental analysis for $C_{41}H_{47}N_3O_{10}$ (741.84): Theory: C: 66.38 H: 6.39N: 5.66% Found: C: 66.09 H: 6.50N: 5.40%

Preparation of the starting compound for Examples 11 and 12

Under nitrogen, 32.4 g (128 mmol) of 11-bromo-1-undecanol are added at 80° C. to a solution of 20.0 g (54 mmol) of 2-phenyl-4,6-bis(2,4-dihydroxyphenyl)-1,3,5-triazine, 6.6 g (109 mmol) of potassium hydroxide and 150 ml of diglyme. The mixture is heated at 100° C. for 14 hours and filtered while hot, and the filtrate is cooled to 0° C. The solid which crystallizes therefrom is filtered off, pressed and dried for 24 hours under reduced pressure (60 mmHg, 60° C.), giving 27.6 g (72% yield) of 2-phenyl-4,6-bis[2-hydroxy-4-(11-hydroxyundecyloxy)phenyl]-1,3,5-triazine as a pale yellow solid of melting point 126°–135° C.

The $^1$H-NMR spectrum ($CDCl_3$, 300 MHz) is in agreement with the desired product.

EXAMPLE 11

Under nitrogen, a mixture of 10.8 g (15 mmol) of 2-phenyl-4,6-bis[2-hydroxy-4-(11-hydroxyundecyloxy)phenyl]-1,3,5-triazine, 3.6 g (40 mmol) of acryloyl chloride, 0.2 g of hydroquinone and 0.3 g (3.8 mmol) of pyridine in 80 ml of toluene is heated at 78° C. for 16 hours. The excess acryloyl chloride and the toluene are removed on a rotary evaporator. The residue is dissolved in 100 ml of toluene, 16.2 g (160 mmol) of triethylamine are added, and the mixture is heated at 80° C. for 5 hours. The mixture is allowed to cool, and the solid residue (($CH_3CH_2)_3$N.HCl) is filtered off. The filtrate is evaporated and then taken up in 50 ml of methylene chloride. The solution is filtered through silica gel (silica gel 60; 230–400 mesh; diameter 6 cm, h=4 cm) and washed with 400 ml of methylene chloride, giving, after the solvent has been stripped off, and the residue dried for 2 hours (80° C./0.1 mmHg), 10.7 g (86% yield) of 2-phenyl-4,6-bis[2-hydroxy-4-(11-acryloyloxyundecyloxy) phenyl]-1,3,5-triazine (compound 203) as a pale yellow solid (melting point 93.3° C., determined by DSC).

The $^1$H-NMR spectrum ($CDCl_3$, 300 MHz) is in agreement with the desired product.

EXAMPLE 12

Under nitrogen, a mixture of 10.8 g (15 mmol) of 2-phenyl-4,6-bis[2-hydroxy-4-(11-hydroxyundecyloxy) phenyl]-1,3,5-triazine, 4.0 g (38 mmol) of methacryloyl chloride, 0.2 g of hydroquinone and 0.3 g (3.8 mmol) of pyridine in 80 ml of toluene is heated at 80°C. for 16 hours. The excess methacryloyl chloride and the toluene are removed on a rotary evaporator. The residue is dissolved in 100 ml of toluene, 8.1 g (80 mmol) of triethylamine and 0.1 g of hydroquinone are added, and the mixture is heated at 70° C. for 4 hours. The mixture is allowed to cool, and the solid residue (($CH_3CH_2)_3$N.HCl) is filtered off. The filtrate is evaporated and then taken up in 50 ml of methylene chloride. The solution is filtered through silica gel (silica gel 60; 230–400 mesh; diameter 6 cm, h=4 cm) and washed with 400 ml of methylene chloride, giving, after the solvent has been stripped off, and the residue dried for 2 hours (80° C./0.1 mmHg), 10.9 g (85% yield) of 2-phenyl-4,6-bis[2-hydroxy-4-(11-methacryloyloxyundecyloxy)phenyl]-1,3,5-triazine (compound 204) as a pale yellow solid (melting point 68.3° C., determined by DSC).

The $^1$H-NMR spectrum ($CDCl_3$, 300 MHz) is in agreement with the desired product.

EXAMPLE 13

Compound (205) is prepared according to the method described in example 11. Tg=17° C.

Analysis: C41H47N3O8 Calc. C 69.37 H 6.67N 5.92% (709.84) Found C 68.53 H 6.67N 6.03%

EXAMPLE 14

Compound (206) is prepared according to the method described in example 11. Tg=15° C.

Analysis: C39H43N3O8 Calc. C 68.71 H 6.36N 6.16% (681.79) Found C 68.65 H 6.44N 6.49%

Intermediate for example 15

2-Phenyl-4-(2-hydroxy-4-n-hexyloxy-phenyl)-6-[2-hydroxy-4-(11-hydroxy-undecyloxy)phenyl]-1,3,5-triazine The reaction is carried out under nitrogen protection.

A mixture of 37.3 g of 2-phenyl-4,6-bis-(2,4-dihydroxy-phenyl)-1,3,5-triazine (0.100 moles), 6.6 g of powdered KOH (Fluka, >85%, 0.100 moles), 25.9 g of 11-bromo-1-undecanol (Fluka, 97%, 0.103 moles), and 0.6 g (3.6 mmoles) of Potassium iodide (Merck, 99.5% ) in 160 mL of diethyleneglycol-dimethyl ether (Diglyme, Fluka, 99% ) is heated under stirring at 110° C. for 4 hours 30 min. After cooling to 50° C., there are added 6.6 g (0.100 moles) of powdered KOH (Fluka, >85%) and 17.0 g (0.103 moles) of n-bromohexane (Fluka, 98%). The mixture is heated at 105° C. under stirring for 14 hours. The mixture is filtered hot and the filtrate evaporated (rotovapor). The product is submitted to a column chromatgraphy [Kieselgel 60, 230–400 mesh; 10 cm diameter; h=30 cm; eluant: $CH_2Cl_2$]. The first eluted product is the di-hexyl-derivative, the second eluted product eluted is the desired title product and the third product is the product dialkylated by two groups 11-hydroxy-undecyl.

After drying at 60° C./60 mmHg for 24 hours, there are obtained 22.5 g (35.8% yield) of 2-phenyl-4-(2-hydroxy-4-n-hexyloxy-phenyl)-6-[2-hydroxy-4-(11-hydroxy-undecyloxy)-phenyl]-1,3,5-triazine, as a pale yellow solid, F. 96°–99° C.

1H NMR (CDCl3, 300 MHz) spectrum is consistent with the desired product.

Analysis C38H49N3O5 Calc. C 72.70 H 7.87N 6.69% (627.83) Found C 72.19 H 8.01N 6.88%

EXAMPLE 15

2-Phenyl-4-(2-hydroxy-4-n-hexyloxy-phenyl)-6-[2-hydroxy-4-(11-methacryloyloxy-undecyloxy)phenyl]-1,3,5-triazine (compound 207)

The reaction is carried out under nitrogen protection.

A mixture of 22.0 g (35.0 mmoles) of 2-phenyl-4-(2-hydroxy-4-n-hexyloxy-phenyl)-6-[2-hydroxy-4-(11-hydroxy-undecyloxy)phenyl]-1,3,5-triazine, 4.4 g (42.0 mmoles) of methacryloyl chloride (Fluka, 97% ), 0.5 g (6.3 mmoles) of pyridine in 100 mL of toluene (Merck, 99.5%) are heated at 80°–85° C. for 21 hours. After cooling to 55° C., there are added 8.9 g (87.5 mmoles) of triethylamine (Fluka, 99.5%). The mixture is heated at 80° C. for further 7 hours then filtered hot. The filtrate is evaporated. The crude product (25.7 g ) is dissolved in 120 mL of $CH_2Cl_2$, filtered through a Kieselgel 60 pad (230–400 mesh; 6.5 cm diameter; h=5 cm) and eluted with 380 mL of CH2Cl2. Solvent removal and drying at 80° C./0.1 mmHg for 2 hours 30 min. give 22.3 g (91.4% yield ) of 2-phenyl-4-(2-hydroxy-4-hexyloxyphenyl)-6-[2-hydroxy-4-(11-methacryloyloxy-undecyloxy)-phenyl]-1,3,5-triazine, as an orange resin, Tg=−13° C. (DSC).

1H NMR (CDCl3, 300 MHz) spectrum is consistent with the desired product.

Analysis C42H53N3O6 Calc. C 72.49 H 7.68N 6.04% (695.90) Found C 72.14 H 7.48N 5.98%

EXAMPLE 16

2-Phenyl-4-[2-hydroxy-4-(11 -acetyloxy-undecyloxy)phenyl]-6-[2-hydroxy-4-(11 -methacryloyloxy-undecyloxy)phenyl]-1,3,5-triazine (compound 208)

The reaction is carried out under nitrogen protection.

A mixture of 20.0 g (28.0 mmol) 2-phenyl-4,6-bis-[2-hydroxy-4-(11-hydroxy-undecyloxy)phenyl]-1,3,5-triazine (intermediate compound for examples 11 and 12), 3.1 g (29.4 mmol) of methacryloyl chloride (Fluka, 97%), 0.2 g of hydroquinone (Fluka, 98%), 0.3 g (3.8 mmol) of pyridine in 115 ml toluene are heated in a first reaction step for 5 hours with stirring at 80° C., followed by cooling to 60° C. and addition of 4.62 g (58.8 mmol) acetic chloride and another 18 hours of heating at 60° C. After separation of the solvent and the excess acetic chloride (rotavap), the residue is dissolved in 100 ml of toluene. Addition of 7.1 g (70 mmol) triethylamine is followed by heating for 6 h with stirring at 70° C. After cooling the solid ($[H_5C_2]_3$N.HCl) is filtered off and the filtrate is concentrated to dryness. The crude product is dissolved in 100 mL of $CH_2Cl_2$, filtered through a layer of Kieselgel 60 (230–400 mesh) and eluted with 1000 mL of $CH_2Cl_2$/Methanol mixture (95:5). Separation of the solvent and drying at 40° C./60 mmHg for 48 h gives 20.8 g (90.1%) of compound (208) as yellow solid, F. 70°–76° C.

EXAMPLE 17

Under nitrogen, a mixture of 7.0 g (14.1 mmol) of 2-(4-chlorophenyl)-4,6-bis[2-hydroxy-4-(2-hydroxyethoxy)phenyl]-1,3,5-triazine, 8.52 g (94.1 mmol) of acryloyl chloride and 0.3 g (3.8 mmol) of pyridine in 180 ml of toluene is heated at 75° C. for 14 hours. The excess acryloyl chloride and the toluene are removed on a rotary evaporator. After addition of 100 ml of toluene and 5.0 g (48 mmol) of triethylamine, the mixture is heated at 90° C. for 14 hours. The mixture is allowed to cool, and the solid residue (($CH_3CH_2)_3$N.HCl) is filtered off. The filtrate is evaporated and recrystallized from ethyl acetate, giving 4.4 g (52% yield) of 2-(4-chlorophenyl)-4,6-bis[2-hydroxy-4-(2-acryloyloxyethoxy)phenyl] -1,3,5-triazine (compound 200) as a yellowish solid (melting point 115°–120° C.).

The $^1$H-NMR spectrum (CDCl$_3$, 300 MHz) is in agreement with the desired product.

Elemental analysis for $C_{31}H_{26}ClN_3O_8$ (604.02): Theory: C: 61.64 H: 4.34 N: 6.96 Cl: 5.87% Found: C: 61.36 H: 4.49 N: 6.98 Cl: 6.02%

Intermediate for Examples 18 to 22b (i) 2-Mesityl-4,6-dichloro-1,3,5-triazine

A solution of 109.5 g (0.55 mol) of 2-bromomesitylene (purity 98%) in 150 ml of abs. THF (purity 99.5%) is added over the course of 1½ hours under nitrogen to a stirred suspension, held at 60° C., of 14.6 g (0.60 mol) of magnesium turnings (purity 99.8%) in 100 ml of abs. THF to which an iodine crystal has been added. The mixture is subsequently kept at the reflux temperature (68° C.) for 30 minutes.

After cooling, the resultant Grignard reagent is transferred into a dropping funnel and added dropwise to a solution of 96.0 g (0.52 mol) of cyanuric chloride (98%) in 270 ml of THF. During the addition, which takes 1½ hours, a temperature of from 15°to 30° C. is maintained by cooling. The mixture is subsequently stirred at 25° C. for 2 hours, then poured into 1 l of an ice/water mixture containing 80 ml of 32% HCl (0.81 mol). The mixture is stirred for one hour and filtered. The filter cake is suspended in 1000 ml of water, stirred for 30 minutes and re-filtered. This operation is repeated twice. The filter cake is dried over $P_2O_5$ for 24 hours at 25° C. and a pressure of 60 mmHg (8000 Pa). 171.0 g of crude product are subsequently dissolved in toluene, filtered while hot and crystallized by the addition of hexane and cooling to 0° C. Filtration and drying give 82.8 g of the title product (i)

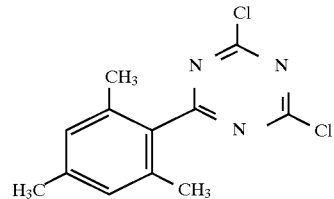

of m.p. 85°–91° C.

$^1$H-NMR (CDCl$_3$, 300 MHz): δ2.22 (s, 6H); 2.32 (s, 3H); 6.95 (s, 2H).

(ii) 2-Mesityl-4,6-bis(2,4-dihydroxyphenyl)-1,3,5-triazine 148.7 g (1.21 mol) of anhydrous aluminium trichloride (purity 98%) are added with stirring to a suspension of 130.0 g (0.485 mol) of 2-mesityl-4,6-dichloro-1,3,5-triazine (i) in 300 ml of petroleum ether with a boiling range of 110°–140° C. and 385 ml of sulfolane. During this addition, the mixture warms to 45° C. A solution of 133.5 e (1.21 mol) of resorcinol (purity 98%) in 155 ml of sulfolane is added to the mixture over the course of 45 minutes. The mixture is warmed at 80°–85° C. for 5 hours 30 minutes with evolution of HCl. The upper phase (petroleum ether) is removed, and the lower, viscous phase is transferred while still hot into a stirred mixture of 2.1 l of methanol and 2.1 l of water. After the mixture has been stirred for 14 hours, the solid is filtered off, stirred in 2.2 l of 1 molar HCl for 1 hour and re-filtered. The filter cake is suspended in 1000 ml of water, stirred for 30 minutes and re-filtered. This operation is repeated twice. The filter cake is dried for 24 hours at 80° C. and a pressure of 60 mmHg (8000 Pa), giving 170.5 g of the title product (ii) of the formula

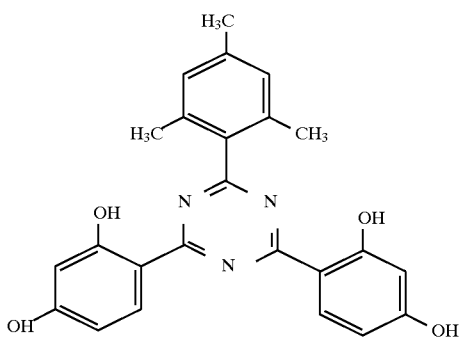

of m.p. 230°–234° C.

EXAMPLE 18

Compound (500) is prepared according to the method described in example 10. It is obtained as yellow resin; Tg.: 9° C.

Analysis (C44H53N3O10): Calc. C 67.42 H 6.81 N 5.36% (783.92) Found C 67.27 H 6.91N 5.66%

EXAMPLE 19

Compound (501) is prepared according to the method described in example 10. It is obtained as 19 yellow resin, Tg.: –2° C.

Analysis (C46H57N3O10): Calc. C 68.04 H 7.08N 5.18% (811.98) Found C 68.01 H 7.10N 4.92%

EXAMPLE 20

Compound (502) is prepared according to the method described in example 12. It is obtained as a resin.

Analysis (C54H73N3O8): Calc. C 72.70 H 8.25N 4.71% (892.19) Found C 71.69 H 8.09N 4.75%

EXAMPLE 21

Compound (503) is prepared according to the method described in examples 9 and 11. It is obtained as yellow resin, Tg.: 22° C.

Analysis (C44H53N3O8): Calc. C 70.28 H 7.11 N 5.59% (751.92) Found C 69.81 H 6.87N 5.67%
Intermediate for examples 22 and 22b 2-Mesityl-4-(2-hydroxy-4-n-hexyloxy-phenyl)-6-[2 -hydroxy-4-(11 -hydroxy-undecyloxy)phenyl]-1,3,5- triazine The reaction is carried out under nitrogen protection.

A mixture of 83.0 g triazine (0.200 moles) of 2-mesityl- 4,6-bis-(2,4-dihydroxy-phenyl)-1,3,5-triazine, 13.2 g (0.200 moles) of powdered KOH (Fluka, >85%), 51.8 g (0.206 moles)of 11-bromo-1-undecanol (Fluka, 97%), and 1.2 g (7.2 mmoles) of Potassium iodide (Merck, 99.5%) in 300 mL of diethylene-glycol-di-methyl ether (Diglyme, Fluka, 99%) is heated under stirring at 120° C. for 3 hours . After cooling to 60° C., there are added 13.2 g of powdered KOH and 34.0 g of n-bromohexane (0.206 moles; Fluka, 98%). The mixture is heated at 110° C. under stirring for 16 hours. The mixture is filtered hot and the filtrate is evaporated (rotovapor). The product (152.1 g) is submitted to a column chromatgraphy [Kieselgel 60; 230–400 mesh); 10 cm diameter; h=30 cm; eluant: toluene/methanol 98:2] to separate the product from the secondary product. The first eluted product is the di-hexyl-derivative, the second product eluted is the desired product and the third product is the product dialkylated by two groups 11-hydroxy-undecyl. After drying at 110° C./0.1 mmHg for 2 hours, there are obtained 55.2 g (41.2% yield ) of 2-mesitylyl-4-(2-hydroxy-4-n-hexyloxy- phenyl)-6-[2-hydroxy-4-(11-hydroxy-undecyloxy)-phenyl]- 1,3,5-triazine, as a yellow resin which crystallises slowly at 25° C.

1H NMR (CDCl3, 300 MHz) spectrum is consistent with the desired product.

Analysis (C41H55N3O5): Calc. C 73.51 H 8.27N 6.27% (669.91) Found C 73.55 H 8.47N 6.29%

EXAMPLE 22

2-Mesityl-4-(2-hydroxy-4-n-hexyloxyphenyl)-6-[2- hydroxy-4-(11-methacryloyl-oxy-undecyloxy)- phenyl]-1,3,5-triazine (compound 504)

The reaction is carried out under nitrogen protection.

A mixture of 10.9 g (16.0 mmoles) of 2-mesityl-4-(2- hydroxy-4-n-hexyloxyphenyl)-6-[2-hydroxy-4-(1 -hydroxy- undecyloxy)-phenyl]-1,3,5-triazine, 2.0 g (19.2 mmoles) of methacryloyl chloride (Fluka, 97%), and 0.4 g (5.0 mmoles) of pyridine in 70 mL of toluene (Merck, 99.5% ) are heated at 80°–85° C. for 16 hours. After cooling to 55° C., there are added 4.1 g (40.0 mmoles) of triethylamine (Fluka, 99.5% ). The mixture is heated at 80° C. for further 6 hours then filtered hot. The filtrate is evaporated. The crude product (13.6 g ) is dissolved in 100 mL of CH2Cl2, filtered through a Kieselgel 60 (230–400 mesh ) pad (6.5 cm diameter; h=4 cm) and eluted with 380mL of CH2Cl2. Solvent removal and drying at 80° C./0.1 mmHg for 2 hours 30 min. gives 22.3 g (91.4% yield) of 2-mesityl-4-(2-hydroxy-4- hexyloxyphenyl)-6-[2-hydroxy-4-(11-methacryloyloxy- undecyloxy)-phenyl]-1,3,5-triazine (compound 504) as a yellow resin; Tg.: –10 ° C. (DSC).

1H NMR (CDCl3, 300 MHz) spectrum is consistent with the desired product.

Analysis (C45H59N3O6): Calc. C 73.24 H 8.06N 5.69% (737.98) Found C 73.01 H 7.76N 5.61%

EXAMPLE 22a

Compound (505) is prepared according to the method described in example 8b. It is obtained as an orange resin; Tg. 13.3° C. (DSC).

Analysis (C42H37N3O4): Calc. C 77.88 H 5.76N 6.49% (647.78) Found C 77.64 H 5.76N 5.66%

EXAMPLE 22b

2-Mesityl-4-(2-hydroxy-4-n-hexyloxyphenyl)-6-[2- hydroxy-4-(11 -acryloyloxy-undecyloxy)-phenyl]-1, 3,5-triazine (compound 506).

The reaction is carried out under nitrogen protection.

A stirred mixture of 27.3 g (40.8 mmoles) of 2-mesityl- 4-(2-hydroxy-4-n-hexyloxyphenyl)-6-[2-hydroxy-4-(11 -hydroxy-undecyloxy)-phenyl]-1,3,5-triazine, 4.4g (49.0 mmoles) of acryloyl chloride (Fluka, 97% ), 0.1 g (0.9 mmoles) of hydroquinone (Fluka, 99% ), and 0.75 g (9.5 mmoles) of pyridine in 170 mL of toluene (Merck, 99.5%) are heated at 70°–75° C. for 17 hours. After cooling to 50° C., there are added 20.0 g (197.6 mmoles) of triethylamine (Fluka, 99.5%). The mixture is heated at 85° C. for further 6 hours then filtered hot. The filtrate is evaporated. The crude product is dissolved in 100 mL of toluene/methanol (98:2), filtered through a Kieselgel 60 (230–400 mesh ) pad (6.5 cm diameter; h=5 cm) and eluted with 400 mL of toluene/methanol (98:2). Solvent removal and drying at 80° C./0.1 mmHg for 3 hours gives 24.3 g (82.3% yield) of 2-mesityl-4-(2-hydroxy-4-hexyloxyphenyl) -6-[2-hydroxy-4-(11-acryloyloxy-undecyloxy)phenyl]-1,3,5-triazine (compound 506) as a yellow resin; Tg. −14.2° C. (DSC).

1H NMR (CDCl3, 300 MHz ) spectrum is consistent with the desired product.

Analysis C44H57N3O6 Calc. C 73.00 H 7.94N 5.80% (723.96) Found C 72.81 H 7.70N 5.53%

EXAMPLE 23

Under nitrogen, a mixture of 15.9 g (20 mmol) of 2,4,6-tris[2-hydroxy-4-(3-n-butoxy-2-hydroxypropoxy)phenyl]-,3,5-triazine, 7.3 g (80 mmol) of acryloyl chloride and 0.4 g (5 mmol) of pyridine in 120 ml of toluene is heated at 75° C. for 24 hours with stirring. The excess acryloyl chloride and the toluene are removed on a rotary evaporator. The residue is dissolved in 100 ml of toluene, 10.1 g (100 mmol) of triethylamine are added, and the mixture is stirred at 80° C. for 6 hours. The mixture is allowed to cool, and the solid residue ((CH$_3$CH$_2$)$_3$N.HCl) is filtered off. The filtrate is evaporated and then taken up in 100 ml of methylene chloride. The solution is filtered through a layer of silica gel (silica gel 60; 230–400 mesh; diameter 10 cm, h=5 cm) and washed with 2000 ml of methylene chloride, giving, after the solvent has been stripped off and the residue dried (90° C./0.5 mmHg), 12.0 g (63% yield) of 2,4,6-tris[2-hydroxy-4-(3-n-butoxy-2-acryloyloxypropoxy)phenyl]-1,3,5-triazine (compound 300) as a pale yellow resin.

The $^1$H-NMR spectrum (CDCl$_3$, 300 MHz) is in agreement with the desired product.

Elemental analysis for C$_{51}$H$_{63}$N$_3$O$_{15}$ (958.07): Theory: C: 63.94 H: 6.63N: 4.39% Found: C: 63.24 H: 6.57N: 4.02%

Preparation of the starting compound for Examples 24 and 25: Under nitrogen, 42.9 g (170 mmol) of 11-bromo-1-undecanol are added at 80° C. to a solution of 20.3 g (50 mmol) of 2,4,6-tris(2,4-dihydroxyphenyl)-1,3,5-triazine, 9.3 g (141 mmol) of potassium hydroxide and 150 ml of diglyme. The mixture is heated at 100° C. for 16 hours and filtered while hot, and the filtrate is cooled to 0° C. The crystallized solid is filtered off, pressed and dried for 48 hours under reduced pressure (60 mmHg, 70° C.), giving 24.3 g (53% yield) of 2,4,6-tris[2-hydroxy-4-(11-hydroxyundecyloxy)phenyl]-1,3,5-triazine as a pale yellow, resin-like solid.

The $^1$H-NMR spectrum (CDCl$_3$, 300 MHz) is in agreement with the desired product.

EXAMPLE 24

Under nitrogen, a mixture of 10.1 g (11 mmol) of 2,4,6-tris[2-hydroxy-4-(11-hydroxyundecyloxy)phenyl]-1,3,5-triazine, 3.6 g (40 mmol) of acryloyl chloride, 0.2 g of hydroquinone and 0.3 g (3.8 mmol) of pyridine in 80 ml of toluene is heated at 80° C. for 18 hours. The excess acryloyl chloride and the toluene are removed on a rotary evaporator. The residue is dissolved in 100 ml of toluene, 16.2 g (160 mmol) of triethylamine and 0.1 g of hydroquinone are added, and the mixture is stirred at 78° C. for 5 hours. The mixture is allowed to cool, and thl solid residue ((CH$_3$CH$_2$)$_3$N.HCl) is filtered off. The filtrate is evaporated and then taken up in 100 ml of methylene chloride. The solution is filtered through a layer of silica gel (silica gel 60; 230–400 mesh; diameter 6 cm; h=4 cm) and washed with 400 ml of methylene chloride, giving, after the solvent has been stripped off, and the residue dried for 2 hours (70° C./0.1 mmHg), 7.7 g (65% yield) of 2,4,6-tris[2-hydroxy-4-(11-acryloyloxyundecyloxy)phenyl]-,1,3,5)-triazine (compound 301) as a pale yellow solid (melting point 72.80° C., determined by DSC).

The $^1$H-NMR spectrum (CDCl$_3$, 300 MHz) is in agreement with the desired product.

EXAMPLE 25

Under nitrogen, a mixture of 10.1 g (11 mmol) of 2,4,6-tris[2-hydroxy-4-(11-hydroxyundecyloxy)phenyl]-1,3,5-triazine, 4.2 g (40 mmol) of methacryloyl chloride, 0.2 g of hydroquinone and 0.3 g (3.8 mmol) of pyridine in 80 ml of toluene is heated at 80° C. for 18 hours. The excess acryloyl chloride and the toluene are removed on a rotary evaporator. The residue is dissolved in 100 ml of toluene, 8.1 g (80 mmol) of triethylamine and 0.1 g of hydroquinone are added, and the mixture is stirred at 70° C. for 5 hours. The mixture is allowed to cool, and the solid residue is filtered off. The filtrate is evaporated and then taken up in 100 ml of methylene chloride. The solution is filtered through a layer of silica gel (silica gel 60; 230–400 mesh; diameter 6 cm; h=4 cm) and washed with 400 ml of methylene chloride, giving, after the solvent has been stripped off, and the residue dried for 2 hours (70° C./0. 1 mmHg), 7.7 g (65% yield) of 2,4,6-tris[2-hydroxy-4-(11-methacryloyloxyundecyloxy)phenyl]-1,3,5-triazine (compound 302) as a pale yellow solid (melting point 60.2° C., determined by DSC).

The $^1$H-NMR spectrum (CDCl$_3$, 300 MHz) is in agreement with the desired product.

EXAMPLE 28

Homopolymer of 2-phenyl-4-(2-hydroxy-4-hexyloxyphenyl)-6-[2-hydroxy-4-(11-methacryloyloxyundecyloxy)phenyl]-1,3,5-triazine (compound 602).

A solution of 5.2 g (7.5 mmol) of 2-(phenyl)-4-(2-hydroxy-4-hexyloxyphenyl)-6-(2-hydroxy-11-methacryloyloxyundecyloxyphenyl)-1,3,5-triazine (compound 207) in 40 ml of toluene (Fluka, 99.5%) is treated, in a 100 ml three-neck flask under argon, with 40 mg (0.22 mmol) of α,α'-azobisisobutyronitrile (AIBN, Fluka 98%) and 70 mg (0.75 mmol) of n-butyl mercaptan (Fluka, 97%). The mixture is kept at 85° C. for 16 hours with stirring. After cooling, the clear yellow solution is added dropwise with stirring to a solution of 400 ml of acetonitrile (Fluka, 99.5%).

The precipitate is decanted and taken up in 30 ml of toluene. Stripping-off of the solvent and drying for 2 hours at 80° C./0.1 mmHg gives 3.35 g (64%) of the title product (compound 602); T$_g$:29.9° C.

1H NMR (CDCl$_3$, 300 MHz) spectrum is consistent with the desired product (no vinyl-H signal).
MALDI-MS
  Mn=1698
  Mw=3251

EXAMPLE 29

Copolymer of 2-phenyl-4-(2-hydroxy-4-hexyloxyphenyl)-6-[2-hydroxy-4-(11-methacryloyloxyundecyloxy)phenyl]-1,3,5-triazine and n-butyl acrylate in the molar ratio 1:4 A solution of 5.2 g (7.5 mmol) of 2-phenyl-4-(2-hydroxy-4-hexyloxyphenyl)-6-(2-hydroxy-11

-methacryloyloxyundecyloxyphenyl)-1,3,5-triazine (compound 207) and 3.8 g (30 mmol) of n-butyl acrylate (Fluka, 99%) in 40 ml of toluene (Fluka, 99.5%) is treated, in a 100 ml three-neck flask under argon, with 200 mg (1.12 mmol) of (α,α'-azobisisobutyronitrile (AIBN, Fluka 98%) and 300mg (3.75 mmol) of n-butyl mercaptan (Fluka, 97%). The mixture is kept at 85° C. for 17 hours with stirring. After cooling, the clear yellow solution is added dropwise with stirring to a solution of 400 ml of acetonitrile (Fluka, 99.5%).

The precipitate is decanted and taken up in 30 ml of toluene; solid impurities are removed by filtration. Stripping-off of the solvent and drying for 2 hours at 80° C./0.1 mmHg gives 6.60 g (73%) of the title product (compound 603); $T_g$: −3.5° C.
MALDI-MS
  Mn=2905
  Mw=4199

EXAMPLE 30

Compound (604) is prepared by the method indicated in Example 28, giving an orange-yellow resin, $T_{g'}$ =49.8° C.

$[C_{45}H_{59}N_3O_6]$ (737.98) calculated C 73.24H 8.06N 5.69% found C 72.57 H 8.43N 5.49%

$M_n$=1920
$M_w$=4198 (MALDI-MS)

EXAMPLE 31

Compound (605) is prepared by the method indicated in Example 29, giving an orange resin, $T_{g'}$ =−4.2 ° C.

$[C_{45}H_{59}N_3O_6]_1[C_7H_{12}O_2]_4$ calculated C 70.11 H 8.62N 3.36% found C 70.71 H 8.74N 3.67%

$M_n$=3238
$M_w$=4923 (MALDI-MS)

EXAMPLE 31a

Compound (606) is prepared by the method indicated in Example 29, but replacing n-butyl acrylate by 30 mmol of n-dodecyl methacrylate; Tg. −33.4° C.
MALDI-MS
  Mn=2023
  Mw=3661

EXAMPLE 32

Compound (607) is prepared by the method indicated in Example 28, giving a white solid.

$[C_{35}H_{39}N_3O_4]$ (565.71) calculated C 74.31H 6.95N 7.43% found C 74.13H 7.16N 7.27%

$M_n$ =1938
$M_w$ =3054 (MALDI-MS)

EXAMPLE 33

Compound (608) is prepared by the method indicated in Example 29.$[C_{35}H_{39}N_3O_4]_1[C_7H_{12}O_2]_4$ calculated C 70.17 H 8.13N 3.90% found C 70.70 H 8.33N 4.60%

$M_n$ =2310
$M_w$ =3341 (MALDI-MS)

EXAMPLE 34

Compound (609) is prepared by the method indicated in Example 28, giving a yellow resin.

$[C_{40}H_{49}N_3O_4]$(635.85) calculated C 75.56 H 7.77N 6.61% found C 74.02 H 8.06N 6.06%

$M_n$ =1781
$M_w$ =3669 (MALDI-MS)

EXAMPLE 35

Compound (610) is prepared by the method indicated in Example 29, but using only half the amount of n-butyl acrylate.

$[C_{40}H_{49}N_3O_4]_1[C_7H_{12}O_2]_2$ calculated C 72.70 H 8.25N 4.71% found C 71.81 H 8.41N 4.68%

$M_n$ =1908
$M_w$ =3111 (GPC)

EXAMPLE 36

Compound (611) is prepared by the method indicated in Example 28, giving a yellow solid of melting point 85.7° C. (DSC).

$[C_{36}H_{41}N_3O_4]$ (579.74) calculated C 74.58 H 7.13N 7.25% found C 73.90 H 7.15N 7.03%

$M_n$ =2405
$M_w$ =3701 (MALDI-MS)

EXAMPLE 37

Compound (612) is prepared by the method indicated in Example 35, giving a yellow resin, $T_g$=15.8° C.

$[C_{36}H_{41}N_3O_4]_1[C_7H_{12}O_2]_2$ calculated C 71.83 H 7.84N 5.03% found C 71.71 H 7.61N 5.19%

$M_n$ =3241
$M_w$ =4920 (MALDI-MS)

EXAMPLE 38

Compound (613) is prepared by the method indicated in Example 28, giving a yellow solid, $T_g$=59.1° C.

$[C_{36}H_{41}N_3O_5]$ (595.74) calculated C 72.58 H 6.94N 7.05% found C 72.25 H 6.95N 6.63%

$M_n$ =2405
$M_w$ =5533 (MALDI-MS)

EXAMPLE 39

Compound (614) is prepared by the method indicated in Example 35, giving an orange resin, $T_g$=35.7° C.

$[C_{36}H_{41}N_3O_5]_1[C_7H_{12}O_2]_2$ calculated C 70.48 H 7.69N 4.93% found C 70.61 H 7.76N 5.35%

$M_n$ =3612
$M_w$ =5264 (MALDI-MS)

EXAMPLE 40

Compound (615) is prepared by the method indicated in Example 35; Tg. 66.5° C.

$M_n$ =2111
$M_w$ =3174 (MALDI-MS)

EXAMPLE 41

Compound (616) is prepared by the method indicated in Example 35; Tg. 59.8° C.

$[C_{34}H_{31}N_3O_2]_1[C_7H_{12}O_2]_2$
$M_n$ =2223
$M_w$ =3634 (MALDI-MS)

EXAMPLE 42

Copolymer of methyl methacrylate and compound (103) Methyl methacrylate is polymerized with 1% by weight of compound No. 103 by the following method:

A mixture of 70.0 g methacrylic acid methylester, 0.7 g of compound (103) and 0.07 g lauroylperoxide is prepolymerized by heating at 60° C. to a syrup-like, still moldable consistency. The prepolymer is given into the mold (2 glass plates 160×210×6 mm, PVC-wire d=1,5 mm, 6 metal clambs), polymerized in a water bath for 6 h at 60° C. and finally cured in a circulating air oven for 3 h at 120° C. Plates of ca. 1.5 mm thichness are obtained.

0.3 g of the resultant modified polymethyl methacrylate (PMMA) are dissolved in $CHCl_3$ (solution I; 0.06 g PMMA/1), and the UV spectrum is measured. The polymer is subsequently precipitated by addition of methanol, filtered off, dried and then re-dissolved in $CHCl_3$ (solution II; 0.04 g PMMA/1). The UV spectrum of solution II is also recorded.

Based on the molecular weight of the monomer, the molar extinction coefficient at 342 nm is calculated:

Solution I: $\epsilon_{342}=20700$

Solution II: $\epsilon_{342}=22200$

The constant extinction coefficient in both solutions shows, that monomer (103) has been incorporated into the polymer.

EXAMPLE 43

Copolymer of methyl methacrylate and compound (402) Methyl methacrylate is polymerized with 1% by weight of compound No. 402 by the method described in example 42. Samples of the polymer obtained are investigated on incorporation of the monomer as described in example 42. The following data are calculated from the UV spectra:

Solution I: $\epsilon_{339}=21600$

Solution II: $\epsilon_{339}=22200$.

The constant extinction coefficient in both solutions shows, that monomer (402) has been incorporated into the polymer.

B) Use examples

B1: Modified PMMA 5 g of modified polymethyl methacrylate from each of Examples 42 and 43 (containing 1% of copolymerized stabilizer [103] and [402] respectively) are dissolved in 30 g, of methylene chloride at room temperature. Films are drawn from this solution onto glass plates, these films having a thickness of 30 μm after evaporation of the solvent and drying in vacuo. For comparative purposes, a similar film is produced from unstabilized polymethyl methacrylate (Plex® 8704, Röhm & Haas, AG).

The films are peeled off from the glass plates and clamped in cardboard frames (6×3 cm). These samples are irradiated in a UV exposure unit with 5 TL/09 fluorescent lamps and 5 TL/12 lamps mounted 20 cm above the samples (wavelength range 295–400 nm). The discolouration of the samples is checked at regular intervals by measuring the Yellowness Index (YI, Method ASTM D 1925). Table 1 shows the results.

TABLE 1

YI of PMMA containing 1% stabilizer in copolymerized form

| Stabilizer | YI before | Irradiation |
|---|---|---|
| none | −0.8 | |
| Comp. (103) | 3.8 | |
| Comp. (402) | 3.2 | |

The stabilizers of the invention cause practically no discoloration of the substrate.

EXAMPLE B6

The novel UV absorbers [compounds (202), (600) and (601)] are predissolved in approx. 5–10 g of xylene and incorporated into a varnish having the following composition:

| | |
|---|---|
| Uracron ® 2263 XB (50%)[1] | 54.5 |
| Cymel ® 327 (90%)[2] | 16.3 |
| Butyl glycol acetate | 5.5 |
| Xylene | 19.4 |
| n-Butanol | 3.3 |
| Baysilon ® A (1% in xylene)[3] | 1 |
| | 100.0 |

[1]Acrylate resin (DSM, NL)
[2]Melamine resin (American Cyanamid, USA)
[3]Flow-control agent (Bayer, D)

The varnish prepared in this way is thinned to sprayable consistency using butyl glycol acetate/n-butanol/xylene (1/6/13) and applied to a prepared substrate (coil coated aluminium sheet, automotive filler, silver-metallic base coat). After a drying time of approx. 15 minutes, the coating is baked at 130° C. for 30 minutes, giving a dry film thickness of approx. 40–45 μm.

The comparison used is a varnish prepared in the same way but containing no UV absorber.

The samples are weathered in a UVCON® unit (Atlas Corp.) (UVB-313 lamps, cycle: 8 h UV, 70° C.; 4 h cond., 50° C.).

The 20° gloss is measured (DIN 67530). The stabilized samples show better gloss retention than the unstabilized comparison sample.

What is claimed is:

1. A polymeric compound obtainable by addition polymerization of a compound of the formula (Id) or a compound of the formula (Id) and a further ethylenically unsaturated compound which is a comonomer selected from the group consisting of acrylic acid, methacrylic acid, acrylates, methacrylates, acrylamides, methacrylamides, vinyl ethers, styrene, styrene derivatives, vinylpyridines, acrylonitrile, methacrylonitrile, vinylpyrrolidone, derivatives of vinylpyrrolidone and ethylenically unsaturated derivatives of sterically hindered amines, 2-(2-hydroxyphenyl)benzotriazoles, 2-hydroxybenzophenones and sterically hindered phenols,

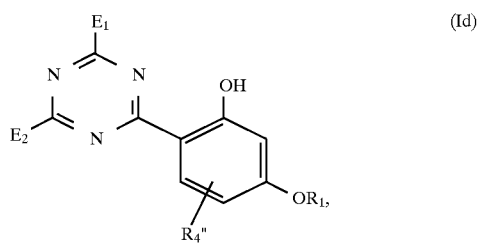

(Id)

in which $E_1$ and $E_2$, independently of one another, are each a group of the formula If or Ig

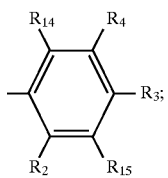
(If)

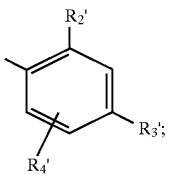
(Ig)

and in which $R_1$, independently of one another, are —$CH_2$—$CH(XA)$—$CH_2$—O—$R_7$, —$CR_8R'_8$—$(CH_2)_l$—XA, —$CH_2$—$CH(OA)$—$R_9$,

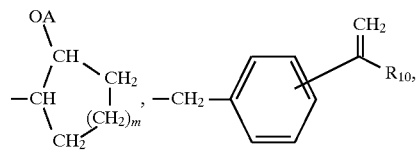

—$CH_2$—$C(=CH_2)$—$R_{10}$, —$(CH_2)_p$—$SiR_{11}R_{11}'$—$CH=CH_2$, —$C(=O)$—$(CH_2)_q$—$CH=CH_2$, —$CHR_8$—$(CH_2)_r$—$C(=O)$—O—$CH_2$—$CH(OH)$—$CH_2$—OA, —$CR_8R'_8$—$(CH_2)_1$—$C(=O)$—XA or —$C(=O)$—O—$CH_2$—$C(=CH_2)$—$R_{10}$; and, in the case where $E_1$ is a group of the formula If in which neither of the radicals $R_2$ and $R_{14}$ is hydrogen, $R_1$ can additionally be —A or —$CH_2$—$CH(OH)$—$CH_2$—XA;

A is —$C(=O)$—$CR_5$=$CH$—$R_6$;

$R_2$, independently of one another, are H, $C_1$–$C_{12}$alkyl, $C_5$–$C_{12}$cycloalkyl, $C_3$–$C_6$alkenyl, halogen, phenyl or trifluoromethyl;

$R_2'$, independently of one another, are $C_1$–$C_{18}$alkoxy, $C_2$–$C_{18}$alkenoxy, —OH or —O—$COR_{12}$;

$R_3$ and $R_3'$, independently of one another, are H, —OH, —$OR_1$, —$OR_{131}$, $C_1$–$C_{18}$alkyl, $C_3$–$C_{18}$alkenyl, $C_6$–$C_{12}$cycloalkyl, halogen, trifluoromethyl, phenyl, phenyl-$C_1$–$C_4$alkyl, —CN, $C_1$–$C_{18}$alkyl-$S(=O)_t$—or phenyl-$S(=O)_t$—;

$R_4$, $R_4'$ and $R_4''$, independently of one another, are H, $C_1$–$C_{18}$alkyl, $C_3$–$C_6$alkenyl, —$OR_{131}$, halogen, trifluoromethyl, phenyl, phenyl-$C_1$–$C_4$alkyl, mono-to tri-$C_1$–$C_4$alkyl-substituted phenyl-$C_1$–$C_4$alkyl, —CN, $C_1$–$C_{18}$alkyl-$S(=O)_t$—or phenyl-$S(=O)_t$—;

$R_5$ is H, —$CH_2$—$COOR_{13}$, $C_1$–$C_4$alkyl or —CN; $R_6$ is H, —$COOR_{13}$, $C_1$–$C_{17}$alkyl or phenyl;

$R_7$ is $C_1$–$C_{18}$alkyl, $C_5$–$C_{12}$cycloalkyl, $C_3$–$C_{18}$alkenyl; phenyl which is substituted by one to three $C_1$–$C_8$alkyl, $C_1$–$C_8$alkoxy, $C_3$–$C_8$alkenoxy, halogen or trifluoromethyl radicals; phenyl-$C_1$–$C_4$alkyl; $C_3$–$C_{50}$alkyl which is interrupted by one or more —O—; 1-adamantyl; 2-adamantyl, norbornyl, 2-methylnorbornyl, —$C(=O)$—$R_{12}$ or —A;

$R_8$ and $R_8'$, independently of one another, are H, $C_1$–$C_{18}$alkyl, phenyl, phenyl-$C_1$–$C_4$alkyl, or phenyl substituted by 1–3 $C_1$–$C_8$alkyl, $C_1$–$C_8$alkoxy, $C_3$–$C_8$alkenoxy, halogen, $CF_3$;

$R_9$ is $C_1$–$C_{18}$alkyl, phenyl or phenyl-$C_1$–$C_4$alkyl; $R_{10}$ is H or —$CH_3$;

$R_{11}$ and $R_{11}'$, independently of one another, are $C_1$–$C_4$alkyl or phenyl or phenyl which is substituted by one to three $C_1$–$C_8$alkyl, $C_1$–$C_8$alkoxy, $C_3$–$C_8$ alkenoxy, halogen or trifluoromethyl radicals;

$R_{12}$ is H, $C_1$–$C_{18}$alkyl, phenyl, phenyl-$C_1$–$C_4$alkyl, $C_5$–$C_{12}$cycloalkyl, $C_1$–$C_{12}$alkoxy, phenoxy, norborn-2-yl, 5-norbornen-2-yl or 1-adamantyl;

$R_{13}$ is H, $C_1$–$C_{18}$alkyl, $C_3$–$C_{18}$alkenyl, phenyl, $C_5$–$C_{12}$cycloalkyl, $C_3$–$C_{50}$alkyl which is interrupted by one or more —O—, phenyl which is substituted by one to three $C_1$–$C_8$alkyl, $C_1$–$C_8$alkoxy, $C_3$–$C_8$alkenoxy, halogen or trifluoromethyl radicals, phenyl-$C_1$–$C_4$alkyl, 2-adamantyl, norbornyl or 2-methylnorbornyl;

$R_{14}$ and $R_{15}$, independently of one another, are H, $C_1$–$C_{18}$alkyl, $C_3$–$C_{18}$alkenyl, $C_6$–$C_{12}$cycloalkyl, halogen, $CF_3$, phenyl, phenyl-$C_1$–$C_4$alkyl, CN, $C_1$–$C_{18}$alkyl-$S(=O)_t$—, phenyl-$S(=O)_t$—or —$OR_{131}$;

$R_{131}$ is $C_1$–$C_{18}$alkyl, $C_1$–$C_{18}$alkyl which is substituted by OH, $C_1$–$C_{18}$alkoxy, $C_5$–$C_{12}$cycloalkoxy, $C_3$–$C_6$alkenyloxy, halogen, —$COOR_{13}$, $CONH_2$, —$COHNR_{132}$, —$CON(R_{132})(R_{133})$, —$NHCOR_{12}$, —CN, —$OCOR_{12}$, phenoxy and/or by phenoxy which is substituted by $C_1$–$C_{18}$alkyl, $C_1$–$C_{18}$alkoxy or halogen, or is $C_3$–$C_{18}$alkenyl, $C_6$–$C_{12}$cycloalkyl, $C_1$–$C_4$alkyl- and/or —$OCOR_{12}$—substituted $C_6$–$C_{12}$cycloalkyl; $C_3$–$C_{50}$alkyl which is interrupted by one or more —O—and may be substituted by OH or —O—$COR_{12}$; phenyl, phenyl-$C_1$–$C_4$alkyl, —$COR_{12}$ or —$SO_2R_{12}$;

$R_{132}$ and $R_{133}$, independently of one another, are $C_1$–$C_{12}$alkyl, $C_3$–$C_{12}$alkoxyalkyl, $C_4$–$C_{16}$dialkylaminoalkyl or $C_5$–$C_{12}$cycloalkyl; or $R_{132}$ and $R_{133}$ together are $C_3$–$C_9$alkylene, $C_3$–$C_9$oxaalkylene or -azaalkylene;

X is —$NR_8$—, —O—, —NH—$(C_nH_{2n})$—NH—or —O—$(C_kH_{2k})$—NH—;

k is a number from 2 to 4;

l is a number from 0 to 19;

m is a number from 2 to 8;

n is a number from 0 to 4;

p is a number from 0 to 10;

q is a number from 1 to 8;

r is a number from 0 to 18; and t is the number 0, 1 or 2.

2. A polymeric compound according to claim 1, obtainable by addition polymerization of a compound of the formula (Ih) or a compound of the formula (Ih) and a further ethylenically unsaturated compound according to claim 1

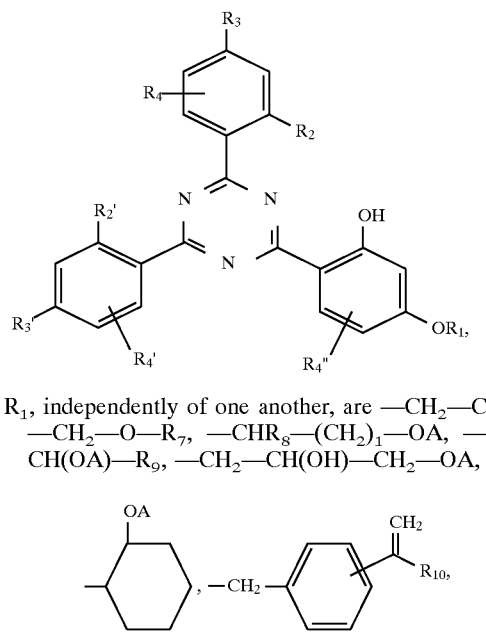

(Ih)

R₁, independently of one another, are —CH₂—CH(OA)—CH₂—O—R₇, —CHR₈—(CH₂)₁—OA, —CH₂—CH(OA)—R₉, —CH₂—CH(OH)—CH₂—OA,

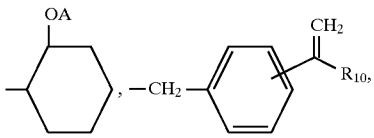

—CH₂—C(=CH₂)—R₁₀, —(CH₂)$_p$—SiR₁₁R₁₁'—CH=CH₂, —C(=O)—(CH₂)$_q$—CH=CH₂, —CHR₈—(CH₂)$_r$—C(=O)—O—CH₂—CH(OH) —CH₂—OA or —C(=O)—O—CH₂—C(=CH₂)—R₁₀; A is —C(=O)—CR₅=CH—R₆;

R₂ and R₂', independently of one another, are H, —OH, —OA, C₁–C₁₂alkyl, cyclohexyl, C₃–C₆alkenyl, C₁–C₁₈alkoxy, C₂–C₁₈alkenoxy, halogen, phenyl or trifuoromethyl;

R₃ and R₃', independently of one another, are H, —OH, —OA, —OR₁, C₁–C₁₂alkyl, cyclohexyl, C₃–C₆alkenyl, C₁–C₁₈alkoxy, C₃–C₁₈alkenoxy, halogen, trifluoromethyl, phenyl, phenoxy, phenyl-C₁–C₄alkyl, phenyl-C₁–C₄alkoxy, —CN, C₁–C₁₈alkyl-S(=O)$_t$—or phenyl-S(=O)$_t$—;

R₄, R₄'and R₄", independently of one another, are H, C₁–C₁₂alkyl, C₃–C₆alkenyl, C₁–C₁₈alkoxy, C₃–C₁₈alkenoxy, halogen, trifluoromethyl, phenyl, phenoxy, phenyl-C₁–C₄alkyl, mono- to tri-C₁–C₄alkyl-substituted phenyl-C₁–C₄alkyl, phenyl-C₁–C₄alkoxy, —CN, C₁–C₁₈alkyl-S(=O)$_t$—or phenyl-S(=O)$_t$—;

R₅ is H, —CH₂—COOR₁₃, C₁–C₄alkyl or —CN;

R₆ is H, —COOR₁₃, C₁–C₁₇alkyl or phenyl;

R₇ is C₁–C₁₈alkyl, cyclohexyl, C₃–C₁₈alkenyl, phenyl, phenyl which is substituted by one to three C₁–C₈alkyl, C₁–C₈alkoxy, C₃–C₈alkenoxy, halogen or trifluoromethyl radicals, phenyl-C₁–C₄alkyl or —C(=O)—R₁₂;

R₈ is H or C₁–C₁₈alkyl;

R₉ is C₁–C₁₈alkyl, phenyl or phenyl-C₁–C₄alkyl;

R₁₀ is H or —CH₃;

R₁₁ and R₁₁', independently of one another, are C₁–C₄alkyl or phenyl or phenyl which is substituted by one to three C₁–C₈alkyl, C₁–C₈alkoxy, C₃–C₈alkenoxy, halogen or trifluoromethyl radicals;

R₁₂ is C₁–C₁₈alkyl, C₂–C₁₈alkenyl or phenyl;

R₁₃ is H, C₁–C₁₈alkyl, C₃–C₁₈alkenyl or phenyl;

l is a number from 0 to 19;

p is a number from 0 to 10;

q is a number from 1 to 8;

r is a number from 0 to 18; and t is the number 0, 1 or 2.

3. A polymeric compound according to claim 1, in which R₁, independently of one another, are —CH₂—CH(XA)—CH₂—O—R₇, —CR₈R₈'—(CH₂)₁—XA,

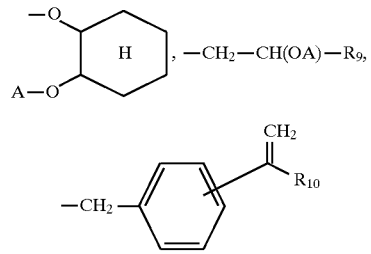, —CH₂—CH(OA)—R₉,

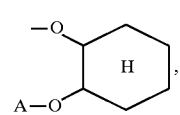

or —CHR₈—(CH₂)$_r$—C(=O)—O—CH₂—CH(OH)—CH₂—OA;

R₂ is H, C₁–C₄alkyl, C₃alkenyl, F, Cl or phenyl;

R₂'is C₁–C₄alkoxy, C₃alkenoxy, —OA, —O—COR₁₂ or —OH;

R₃ and R₃', independently of one another, are H, —OH, —OR₁, —OR₁₃₁, C₁–C₄alkyl, cyclohexyl, C₃alkenyl, F, Cl, trifluoromethyl, phenyl, benzyl or —CN;

R₄'and R₄", independently of one another, are H, C₁–C₄alkyl, C₃alkenyl, C₁–C₄alkoxy, C₃alkenoxy, F, Cl, trifluoromethyl, phenyl, phenyl-C₁–C₃alkyl or —CN;

R₅ is H or —CH₃;

R₆ is H, —COOR₁₃, —CH₃ or phenyl;

R₇ is C₁–C₈alkyl, cyclohexyl, C₃–C₈alkenyl, phenyl, phenyl which is substituted by one to three C₁–C₄alkyl or C₁–C₄alkoxy radicals, or benzyl;

R₈ and R₈', independently of one another, are H or C₁–C₁₈alkyl;

R₉ is C₁–C₁₀alkyl, phenyl or benzyl;

R₁₂ is H, C₁–C₁₈alkyl, phenyl, phenyl-C₁–C₄alkyl or cyclohexyl;

R₁₃ is C₁–C₄alkyl, C₃alkenyl, cyclohexyl, phenyl-C₁–C₄alkyl or phenyl;

R₄, R₁₄ and R₁₅, independently of one another, are H, F, Cl, C₁–C₄alkoxy, CF₃, phenyl, CN or C₁–C₈alkyl;

R₁₃₁ is C₁–C₁₈alkyl, C₃–C₁₈alkyl which is substituted by OH, C₁–C₁₈alkoxy, C₅–C₁₂cycloalkoxy, —COOR₁₃, —CONH₂, —COHNR₁₃₂, —CON(R₁₃₂)(R₁₃₃), —NHCOR ₁₂, —CN, —OCOR₁₂ and/or phenoxy, or is C₃alkenyl, C₆–C₁₂cycloalkyl; C₃–C₅₀alkyl which is interrupted by one or more —O— and may be substituted by OH or O—COR₁₂; phenyl, phenyl—C₁–C₄alkyl, —COR₁₂ or —SO₂R₁₂;

X is —O— or —NR₈—;

l is a number from 1 to 19; and r is a number from 0 to 10.

4. A polymeric compound according to claim 1, in which R₁ independently of one another, are —CH₂—CH(OA)—CH₂—O—R₇, —CH₂—CH(OA)—R₉, -continued

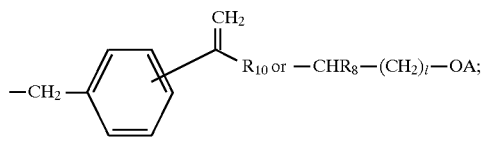

or —CHR₈—(CH₂)₁—OA; A is —C(=O)—CR₅=CH—R₆

R₂ is H, —CH₃, —OCH₃, C₃alkenoxy or Cl;
R₂' is —OH;
R₃ is H, —CH₃, C₁–C₄alkoxy, C₃alkenoxy, F, Cl, phenyl, benzoxy or —CN;
R₃' is —OR₁ or —OR₁₃₁;
R₄, R₁₄ and R₁₅, independently of one another, are H, F, Cl, Phenyl, CH, OCH₃ or CH₃;
R₄' and R₄", independently of one another, are H, —CH₃, C₃alkenyl, —OCH₃, C₃alkenoxy, F, Cl, phenyl-C₃alkyl or —CN;
R₅ is H or —CH₃;
R₆ is H or —CH₃;
R₇ is C₁–C₈alkyl, cyclopentyl, cyclohexyl, C₃alkenyl, phenyl or benzyl;
R₈ is H or C₁–C₁₈alkyl;
R₉ is C₁–C₁₀alkyl or phenyl;
R₁₂ is C₁–C₁₈alkyl, phenyl or cyclohexyl;
R₁₃₁ is C₁–C₁₈alkyl or C₃–C₁₈alkyl which is substituted by C₁–C₁₈alkoxy, OH, phenoxy, —NHCOR₁₂ and/or —OCOR₁₂; and
l is a number from 1 to 19.

5. A polymeric compound according to claim 1, in which R₁, independently of one another, are —CH₂—CH(OA)—CH₂—O—R₇, —CH₂—CH(OA)—R₉,

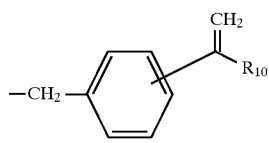

or —CH₂—(CH₂)ₗ—OA;
A is —C(=O)—CR₅=CH—R₆
R₂ is H or CH₃;
R₂' is —OH;
R₃ is H, —CH₃, Cl or phenyl;
R₃' is —OR₁ or —OR₁₃₁;
R₄ is H or CH₃;
R₄', R₄", R₁₄ and R₁₅ are hydrogen;
R₅ is H or —CH₃;
R₆ is H;
R₇ is C₁–C₈alkyl;
R₉ is C₁–C₁₀alkyl;
R₁₂ is C₁–C₈alkyl;
R₁₃₁ is C₃–C₁₈alkyl or C₃–C₁₈alkyl which is substituted by —OCOR₁₂; and
l is a number from 1 to 10.

6. A polymeric compound according to claim 1, in which a further comonomer conforms to one of formulae (II)–(VII):

R₁₈—CH=C(R₁₇)—C(=O)—X'—R₂₀, (II)

in which X' is —O— or —NR₁₉—;
R₁₇ is H, C₁–C₄alkyl, —CH₂—COOR₂₁, —Cl or —CN;
R₁₈ is H, —COOR₂₁ or —CH₃;
R₁₉ is H, C₁–C₈alkyl, C₄–C₁₂cycloalkyl, —N(Rₓ)₂-substituted C₁–C₄alkyl, -S(=O)—Rₓ, —C(CH₃)₂—CH₂—C(=O)—CH₃, —C(CH₃)₂—CH₂—SO₃M, —(CH₂)ₛ—SO₃M or

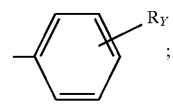

R₂₀ is H, C₁–C₁₈alkyl, C₃–C₁₈alkenyl, C₂–C₃₀alkyl which is interrupted by one or more O atoms and can be substituted by OH, or is —(CH₂)ₛ—SO₃M,

—CH₂F, —CH₂Cl, —CH₂CN, —CH₂CH₂Cl, —CH₂CH₂CN, —CH₂CH₂—COORₓ, C₇–C₁₁phenylalkyl, naphthyl, —N(Rₓ)₂-substituted C₁–C₄alkyl, adamantyl or C₆–C₁₂cycloalkyl;

R₂₁ is H, C₁–C₁₈alkyl, phenyl or C₃–C₁₈alkenyl;
Rₓ is C₁–C₄alkyl or phenyl;
Rᵧ is H, C₁–C₁₂alkyl, phenyl, —CO—ORₓ, —CN, —F, or —Cl;
M is H or an alkali metal; and
s is a number from 1 to 5;

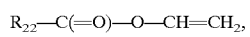 (III)

in which R₂₂ is C₁–C₁₉alkyl or phenyl;

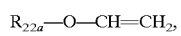 (IIIa)

in which R₂₂ₐ is C₁–C₁₈alkyl;

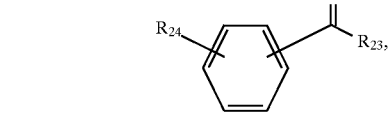 (IV)

in which R₂₃ is H or —CH₃;
R₂₄ is H, —CR₂₃=CH₂, —C(O)—phenyl or —SO₃M; and
M is H or an alkali metal;

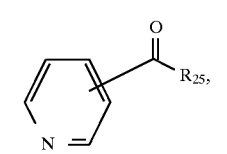 (V)

in which R₂₅ is H or —CH₃;

 (VI)

in which R₂₆ is H, —F, —Cl or —CH₃ and $R_{27}$ is —Cl, —Br, —F or —CN;

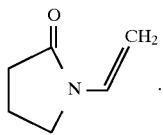 (VII)

7. A polymeric compound according to claim 6, obtainable by copolymerization of a compound of the formula (Id) and a further comonomer of one of the formulae (II)–(IV) and (VII) according to claim 6,
where
$R_{17}$ is H or —CH$_3$;
$R_{18}$ is H or —CH$_3$;
$R_{19}$ is H, $C_1$–$C_4$alkyl, —C(CH$_3$)$_2$—CH$_2$—SO$_3$M or —(CH$_2$)$_s$—SO$_3$M;
$R_{20}$ is H, $C_1$–$C_8$alkyl, or $C_2$–$C_{20}$alkyl which is interrupted by one or more O atoms;
$R_{22}$ is —CH$_3$;
$R_{22a}$ is $C_1$–$C_4$alkyl;
$R_{23}$ and $R_{24}$ are H;
M is H, Li, Na or K;
X is —O— or —NR$_{19}$—; and
s is the number 2 or 3.

* * * * *